(12) United States Patent
Hefeneider et al.

(10) Patent No.: US 8,318,680 B2
(45) Date of Patent: Nov. 27, 2012

(54) METHOD AND PEPTIDE FOR REGULATING CELLULAR ACTIVITY

(75) Inventors: Steven H. Hefeneider, Portland, OR (US); Sharon L. McCoy, Portland, OR (US)

(73) Assignees: The United States of America, as represented by the U.S. Department of Veterans Affairs, Washington, DC (US); Oregon Health & Science University, Portland, OR (US)

( * ) Notice: Subject to any disclaimer, the term of this patent is extended or adjusted under 35 U.S.C. 154(b) by 0 days.

(21) Appl. No.: 13/284,698

(22) Filed: Oct. 28, 2011

(65) Prior Publication Data

US 2012/0039922 A1    Feb. 16, 2012

Related U.S. Application Data

(60) Continuation of application No. 12/479,645, filed on Jun. 5, 2009, now Pat. No. 8,071,553, which is a division of application No. 11/656,512, filed on Jan. 23, 2007, now Pat. No. 7,557,086, which is a division of application No. 11/178,316, filed on Jul. 12, 2005, now Pat. No. 7,192,930.

(60) Provisional application No. 60/586,701, filed on Jul. 12, 2004.

(51) Int. Cl.
*A61K 38/08* (2006.01)
*A61K 38/19* (2006.01)

(52) U.S. Cl. ............... 514/21.6; 530/327; 424/158.1

(58) Field of Classification Search .................. None
See application file for complete search history.

(56) References Cited

U.S. PATENT DOCUMENTS

| 7,192,930 B2 | 3/2007 | Hefeneider et al. |
| 7,557,086 B2 | 7/2009 | Hefeneider et al. |
| 2005/0244430 A1 | 11/2005 | O'Neill et al. |
| 2011/0053830 A1 | 3/2011 | Hefeneider et al. |

OTHER PUBLICATIONS

Gerards, 2003, Rheumatology, 42, 1189-1196.*
Bowie, 2000, PNAS, 97, 10162-10167.*
Akira, "Mammalian Toll-like receptors," *Curr. Opin, Immunol.*, 15:5-11, (2003).
Almawi and Melemedjian, "Negative regulation of nuclear factor-kappaB activation and function by glucocorticoids," *J. Mol. Endocrinol.*, 28:69-78, (2002).
Andreakos et al., "Cytokines and anti-cytokine biologicals in autoimmunity: present and future," *Cytokine Growth Factor Rev.*, 13:299-313, (2002).
Bartfai et al., "A low molecular weight mimic of the Toll/IL-1 receptor/resistance domain inhibits IL-1 receptor-mediated responses," *Proc. Natl. Acad. Sci. U.S.A.*, 100:7971-7976, (2003).
Barton and Medzhitov, "Linking Toll-like receptors to IFN-α/β expression," *Nat. Immunol.*, 4:432-433, (2003).
Barzilai et al., "Middle ear effusion II-6 concentration in bacterial and non-bacterial acute otitis media," *Acta Paediatr*, 89:1068-1071, (2000).
Basu and Fenton, "Toll-like receptors: function and roles in lung disease," *Am. I Physiol. Lung Cell Mol. Physiol.* 286:L887-892, (2004).
Bellows et al., "Vaccinia virus-induced inhibition of nitric oxide production," *J. Surg. Res.*, 111:127-135, (2003).
Bone et al., "Definitions for sepsis and organ failure and guidelines for the use of innovative therapies in sepsis," *Chest*, 101:1644-1655, (1992).
Bowie et al., "A46R and A52R from vaccinia virus are antagonists of host IL-1 and toll-like receptor signaling," *Proc. Natl. Acad. Sci. U.S.A.*, 97:10162-10167, (2000).
Brint et al., "ST2 is an inhibitor of interleukin 1 receptor and Toll-like receptor 4 signaling and maintains endotoxin tolerance," *Nat. Immunol.*, 5:373-379, (2004).
Chuang and Ulevitch, "Triad3A, an E3 ubiquitin-protein ligase regulating Toll-like receptors," *Nat. Immunol.*, 5:495-502, (2004).
Daly et al., "Chronic Otitis Media with Effusion," *Pediatrics in Review*, 20:85-93, (1999).
Daun and Fenton, "Interleukin-1fToll receptor family members: receptor structure and signal transduction pathways," *J. Interferon Cytokine Res.*, 20:843-855, (2000).
Delgado et al., "PACAP in immunity and inflammation," *Ann. N. Y. Acad. Sci.*, 992: 141-157, (2003).
Fan and Malik Toll-like receptor-4(TLR4) signaling augments chemokine-induced neutrophil migration by modulating cell surface expression of chemokine receptors, *Nat. Med.*, 9:315-321, (2003).
Granucci et al., "Inducible Il-2 production by dendritic cells revealed by global gene expression analysis," *Nat. Immunol.*, 2:882-888, (2001).
Harte et al., "The poxvirus protein A52R targets Toll-like receptor signaling complexes to suppress host defense," *J. Exp. Med.*, 197:343-351, (2003).
Hayashi et al., "The innate immune response to bacterial flagellin is mediated by Toll-like receptor 5," *Nature* 410: 1 099-11 03, (2001).
Hemmi et al., "A Toll-like receptor recognizes bacterial DNA," *Nature*, 408:740-745, (2000).
Hoshino et al., "Cutting Edge: Toll-like receptor 4 (TLR4)-deficient mice are hyperresponsive to lipopolysaccharide: evidence for TLR4 as the Lps gene product," *J. Immunol.*, 162: 3749-3752, (1999).
Ikezoe et al., PC-SPES: A potent inhibitor of nuclear factor-kB rescues mice from lipopolysaccharide-induced septic shock, *Mol. Pharmacol.*, 64:1521-1529, (2003).

(Continued)

Primary Examiner — Karlheinz R Skowronek
Assistant Examiner — Satyanarayana R Gudibande
(74) Attorney, Agent, or Firm — Klarquist Sparkman, LLP

(57) ABSTRACT

Method and peptide for regulating cellular activity includes a panel of synthesized peptides that have biological effects on inhibiting or enhancing cellular activity. Selected peptides can be used as therapy to reduce and/or inhibit, or initiate and/or enhance, an inflammatory response in a subject.

20 Claims, 22 Drawing Sheets

OTHER PUBLICATIONS

Janssens and Beyaert, "Functional diversity and regulation of different interleukin-1 receptor-associated kinase (IRAK) family members," *Mol. Cell.*, 11:293-302, (2003).

Karasen et al., "Effect of web 2170 BS, platelet activating factor receptor inhibitor, in the guinea pig model of middle ear inflammation," *Ann. Otol. Rhiniol Laryngol.*, 109:549-553, (2000).

Kopp and Ghosh, "Inhibition of NF-kappa B by sodium salicylate and aspirin," *Science*, 265:956-959, (1994).

Krieg, "CpG motifs in bacterial DNA and their immune effects," *Ann. Rev. Immunol.* 20:709-760, (2002).

Kubba et al., "The aetiology of otitis media with effusion: a review," *Clin. Otolaryngol*, 25:181-194, (2000).

McCoy et al., "Activation of RAW264.7 macrophages by bacterial DNA and lipopolysaccharide increases cell surface DNA binding and internalization," *J. Biol. Chem.*, 279:17217-17223, (2004).

McCoy et al., "Identification of a Peptide Derived form Vaccinia Virus A52R Protein That Inhibits Cvtokine Secretion in Response to TLR-Dependent Signaling and Reduces In Vivo Bacterial-Induced Inflammation," *The Journal of Immunology*, 174:3006-3014, (2005).

Meng et al., "Antagonistic antibody prevents Toll-like receptor 2-driven lethal shock-like syndromes," *J. Clin. Invest.*, 113:1473-1481, (2004).

Ng and Henikoff, "Predicting Deleterious Amino Acid Substitutions," *Genome Research*, 11:863-874, (2001).

O'Brien, "SEPSIS," *The American Journal of Medicine*, 120:1012-1022, (2007).

O'Neill, "The Toll/interleukin-1 receptor domain: a molecular switch for inflammation and host defense," *Biochem. Soc. Trans.*, 28:557-563, (2000).

Office action, dated Mar. 20, 2008, from co-pending U.S. Appl. No. 11/834,506.

Office action, dated Nov. 26, 2008, from co-pending U.S. Appl. No. 11/834,506.

O'Neill, "Therapeutic targeting of Toll-like receptors for inflammatory and infectious diseases," *Curr. Opin. Pharm.*, 3:396-403, (2003).

Ozato et al., "Toll-like receptor signaling and regulation of cytokine gene expression in the immune system," *BioTechniques*, Oct. Suppl: 66-75, (2002).

Rittirsch et al., "The disconnect between animal models of species and human sepsis," *The Journal of Leukocyte Biology*, 81:137-143, (2007).

Schnare et al., "Toll-like receptor control activation of adaptive immune responses," *Nat. Immuno.*, 2:947-950, (2001).

Sweet et al., "A novel pathway regulating lipopolysaccharide-induced shock by ST2/T1 via inhibition of Toll-like receptor 4 expression," *J. Immunol.*, 166:6633-6639, (2001).

Takeda and Akira, "TLR signaling pathways," *Semin. Immunol,*, 16:3-9, (2004).

Takeda et al., "Toll-like receptors," *Ann. Rev. Immunol.* 21:335-378, (2003).

Trinchieri, "Interleukin-12: a cytokine at the interface of inflammation and immunity," *Adv. Immunol.*, 70:83-243, (1998).

Tsung et al., "A novel inhibitory peptide of toll-like receptor signaling limits lipopolysaccharide-induced produced of inflammatory mediators and enhances survival in mice," *Shock*, 27(4):364-369, (2007).

Voet and Voet., *Biochemistry*, 2nd Edition., 235-241, (1995).

Wender et al., "The design, synthesis, and evaluation of molecules that enable or enhance cellular uptake: Peptoid molecular transporters," *Proc. Nat. Acad. Sci. U.S.A.*, 97:13003-13008, (2000).

Yi and Krieg. "Cutting Edge: Rapid induction of mitogen-activated protein kinases by immune stimulatory CpG DNA," *J. Immunol.*, 161:4493-4497, (1998).

Yi et al., "Role of mitogen-activated protein kinases in CpG DNA-mediated IL-10 and IL-12 production: central role of extracellular Signal-regulated kinase in the negative feedback loop of the CpG DNA-mediated Th1 response," *J. Immunol.*, 168:4711-4720, (2002).

Zuany-Amorim et al., "Toll-like receptors as potential therapeutic targets for multiple diseases," *Nat. Rev, Drug Discov.*, 1:797-807, (2002).

* cited by examiner

Peptide #1 (NH₂-terminal)- Met-Asp-Ile-Lys-Ile-Asp-Ile-Ser-Ser-Gly-Asp-Lys-Phe-Thr-Val-Thr-(OH-terminal) (SEQ ID NO: 1)

Peptide #2 (NH₂-terminal)- Gly-Asp-Lys-Phe-Thr-Val-Thr-Arg-Arg-Glu-Asn-Glu-Glu-Arg-Lys-Lys-Tyr-(OH-terminal) (SEQ ID NO: 2)

Peptide #3 (NH₂-terminal)- Asn-Glu-Glu-Arg-Lys-Lys-Tyr-Leu-Pro-Leu-Glu-Lys-Glu-Lys-Thr-Thr-Asp-(OH-terminal) (SEQ ID NO: 3)

Peptide #4 (NH₂-terminal)- Glu-Lys-Glu-Lys-Thr-Thr-Asp-Val-Ile-Lys-Pro-Asp-Tyr-Leu-Glu-Tyr-(OH-terminal) (SEQ ID NO: 4)

Peptide #5 (NH₂-terminal)- Lys-Pro-Asp-Tyr-Leu-Glu-Tyr-Asp-Leu-Leu-Asp-Arg-Asp-Glu-Met-Phe-(OH-terminal) (SEQ ID NO: 5)

Peptide #6 (NH₂-terminal)- Leu-Asp-Arg-Asp-Glu-Met-Phe-Thr-Ile-Leu-Glu-Gln-Tyr-Phe-Met-Tyr-Arg-(OH-terminal) (SEQ ID NO: 6)

Peptide #7 (NH₂-terminal)- Glu-Gln-Tyr-Phe-Met-Tyr-Arg-Gly-Leu-Arg-Ile-Lys-Tyr-Gly-(OH-terminal) (SEQ ID NO: 7)

Peptide #8 (NH₂-terminal)- Gly-Leu-Arg-Ile-Lys-Tyr-Gly-Arg-Leu-Phe-Asn-Gln-Ile-Lys-Lys-Phe-Asp-(OH-terminal) (SEQ ID NO: 8)

Peptide #9 (NH₂-terminal)- Asn-Gln-Ile-Lys-Lys-Phe-Asp-Asp-Asn-Ala-Glu-Gln-Phe-Gly-Thr-Ile-(OH-terminal) (SEQ ID NO: 9)

Peptide #10 (NH₂-terminal)- Glu-Gln-Phe-Gly-Thr-Ile-Gln-Gln-Leu-Lys-Gln-Lys-Leu-Arg-Leu-Asn-(OH-terminal) (SEQ ID NO: 10)

Peptide #11 (NH₂-terminal)- Lys-Leu-Arg-Leu-Asn-Ser-Glu-Gln-Gly-Ala-Asp-(OH-terminal) (SEQ ID NO: 11)

Peptide #12 (NH₂-terminal)- Asn-Phe-Ile-Asp-Tyr-Ile-Lys-Val-Gln-Lys-Gln-(OH-terminal) (SEQ ID NO: 12)

FIG. 19A

Peptide #13 (NH₂-terminal)- Asp-Ile-Val-Lys-Leu-Thr-Val-Tyr-Asp-Cys-Ile -(OH-terminal) (SEQ ID NO: 13)

Peptide #14 (NH₂-terminal)- Ser-Met-Ile-Gly-Leu-Cys-Ala-Cys-Val-Val-Asp -(OH-terminal) (SEQ ID NO: 14)

Peptide #15 (NH₂-terminal)- Val-Trp-Arg-Asn-Glu-Lys-Leu-Phe-Ser-Arg-Trp -(OH-terminal) (SEQ ID NO: 15)

Peptide #16 (NH₂-terminal)- Lys-Tyr-Cys-Leu-Arg-Ala-Ile-Lys-Leu-Phe-Ile -(OH-terminal) (SEQ ID NO: 16)

Peptide #17 (NH₂-terminal)- Asn-Asp-His-Met-Leu-Asp-Lys-Ile-Lys-Ser-Ile -(OH-terminal) (SEQ ID NO: 17)

Peptide #18 (NH₂-terminal)- Leu-Gln-Asn-Arg-Leu-Val-Tyr-Val-Glu-Met-Ser -(OH-terminal) (SEQ ID NO: 18)

FIG. 19B

SEQUENCE LISTING

<160> NUMBER OF SEQ ID NOS: 22

<210> SEQ ID NO 1
<211> LENGTH: 17
<212> TYPE: PRT
<213> ORGANISM: Artificial sequence
<220> FEATURE:
<223> OTHER INFORMATION: Synthetic Polypeptide

<400> SEQUENCE: 1

Met Asp Ile Lys Ile Asp Ile Ser Ile Ser Gly Asp Lys Phe Thr Val
1               5                   10                  15

Thr

<210> SEQ ID NO 2
<211> LENGTH: 18
<212> TYPE: PRT
<213> ORGANISM: Artificial sequence
<220> FEATURE:
<223> OTHER INFORMATION: Synthetic Polypeptide

<400> SEQUENCE: 2

Gly Asp Lys Phe Thr Val Thr Thr Arg Arg Glu Asn Glu Glu Arg Lys
1               5                   10                  15

Lys Tyr

<210> SEQ ID NO 3
<211> LENGTH: 17
<212> TYPE: PRT
<213> ORGANISM: Artificial sequence
<220> FEATURE:
<223> OTHER INFORMATION: Synthetic Polypeptide

<400> SEQUENCE: 3

Asn Glu Glu Arg Lys Lys Tyr Leu Pro Leu Gln Lys Gly Lys Thr Thr
1               5                   10                  15

Asp

<210> SEQ ID NO 4
<211> LENGTH: 16
<212> TYPE: PRT
<213> ORGANISM: Artificial sequence
<220> FEATURE:
<223> OTHER INFORMATION: Synthetic Polypeptide

<400> SEQUENCE: 4

Gln Lys Gly Lys Thr Thr Asp Val Ile Lys Pro Asp Tyr Leu Glu Tyr
1               5                   10                  15

<210> SEQ ID NO 5
<211> LENGTH: 17
<212> TYPE: PRT
<213> ORGANISM: Artificial sequence
<220> FEATURE:
<223> OTHER INFORMATION: Synthetic Polypeptide

<400> SEQUENCE: 5

Lys Pro Asp Tyr Leu Glu Tyr Asp Asp Leu Leu Asp Arg Asp Glu Met
1               5                   10                  15

Phe

<210> SEQ ID NO 6
<211> LENGTH: 17

```
<212> TYPE: PRT
<213> ORGANISM: Artificial sequence
<220> FEATURE:
<223> OTHER INFORMATION: Synthetic Polypeptide

<400> SEQUENCE: 6

Leu Asp Arg Asp Glu Met Phe Thr Ile Leu Glu Glu Tyr Phe Met Tyr
1               5                   10                  15

Arg

<210> SEQ ID NO 7
<211> LENGTH: 17
<212> TYPE: PRT
<213> ORGANISM: Artificial sequence
<220> FEATURE:
<223> OTHER INFORMATION: Synthetic Polypeptide

<400> SEQUENCE: 7

Glu Glu Tyr Phe Met Tyr Arg Gly Leu Leu Gly Leu Arg Ile Lys Tyr
1               5                   10                  15

Gly

<210> SEQ ID NO 8
<211> LENGTH: 17
<212> TYPE: PRT
<213> ORGANISM: Artificial sequence
<220> FEATURE:
<223> OTHER INFORMATION: Synthetic Polypeptide

<400> SEQUENCE: 8

Gly Leu Arg Ile Lys Tyr Gly Arg Leu Phe Asn Glu Ile Lys Lys Phe
1               5                   10                  15

Asp

<210> SEQ ID NO 9
<211> LENGTH: 17
<212> TYPE: PRT
<213> ORGANISM: Artificial sequence
<220> FEATURE:
<223> OTHER INFORMATION: Synthetic Polypeptide

<400> SEQUENCE: 9

Asn Glu Ile Lys Lys Phe Asp Asn Asp Ala Glu Glu Gln Phe Gly Thr
1               5                   10                  15

Ile

<210> SEQ ID NO 10
<211> LENGTH: 17
<212> TYPE: PRT
<213> ORGANISM: Artificial sequence
<220> FEATURE:
<223> OTHER INFORMATION: Synthetic Polypeptide

<400> SEQUENCE: 10

Glu Glu Gln Phe Gly Thr Ile Glu Glu Leu Lys Gln Lys Leu Arg Leu
1               5                   10                  15

Asn

<210> SEQ ID NO 11
<211> LENGTH: 11
<212> TYPE: PRT
<213> ORGANISM: Artificial sequence
<220> FEATURE:
<223> OTHER INFORMATION: Synthetic Polypeptide
```

```
<400> SEQUENCE: 11

Lys Leu Arg Leu Asn Ser Glu Glu Gly Ala Asp
1               5                   10

<210> SEQ ID NO 12
<211> LENGTH: 11
<212> TYPE: PRT
<213> ORGANISM: Artificial sequence
<220> FEATURE:
<223> OTHER INFORMATION: Synthetic Polypeptide

<400> SEQUENCE: 12

Asn Phe Ile Asp Tyr Ile Lys Val Gln Lys Gln
1               5                   10

<210> SEQ ID NO 13
<211> LENGTH: 11
<212> TYPE: PRT
<213> ORGANISM: Artificial sequence
<220> FEATURE:
<223> OTHER INFORMATION: Synthetic Polypeptide

<400> SEQUENCE: 13

Asp Ile Val Lys Leu Thr Val Tyr Asp Cys Ile
1               5                   10

<210> SEQ ID NO 14
<211> LENGTH: 11
<212> TYPE: PRT
<213> ORGANISM: Artificial sequence
<220> FEATURE:
<223> OTHER INFORMATION: Synthetic Polypeptide

<400> SEQUENCE: 14

Ser Met Ile Gly Leu Cys Ala Cys Val Val Asp
1               5                   10

<210> SEQ ID NO 15
<211> LENGTH: 11
<212> TYPE: PRT
<213> ORGANISM: Artificial sequence
<220> FEATURE:
<223> OTHER INFORMATION: Synthetic Polypeptide

<400> SEQUENCE: 15

Val Trp Arg Asn Glu Lys Leu Phe Ser Arg Trp
1               5                   10

<210> SEQ ID NO 16
<211> LENGTH: 11
<212> TYPE: PRT
<213> ORGANISM: Artificial sequence
<220> FEATURE:
<223> OTHER INFORMATION: Synthetic Polypeptide

<400> SEQUENCE: 16

Lys Tyr Cys Leu Arg Ala Ile Lys Leu Phe Ile
1               5                   10

<210> SEQ ID NO 17
<211> LENGTH: 11
<212> TYPE: PRT
<213> ORGANISM: Artificial sequence
<220> FEATURE:
<223> OTHER INFORMATION: Synthetic Polypeptide

<400> SEQUENCE: 17
```

```
Asn Asp His Met Leu Asp Lys Ile Lys Ser Ile
1               5                   10

<210> SEQ ID NO 18
<211> LENGTH: 11
<212> TYPE: PRT
<213> ORGANISM: Artificial sequence
<220> FEATURE:
<223> OTHER INFORMATION: Synthetic Polypeptide

<400> SEQUENCE: 18

Leu Gln Asn Arg Leu Val Tyr Val Glu Met Ser
1               5                   10

<210> SEQ ID NO 19
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 19
tccatgacgt tcctgacgtt                                                   20

<210> SEQ ID NO 20
<211> LENGTH: 20
<212> TYPE: PRT
<213> ORGANISM: Artificial sequence
<220> FEATURE:
<223> OTHER INFORMATION: Synthetic Polypeptide

<400> SEQUENCE: 20

Asp Ile Val Lys Leu Thr Val Tyr Asp Cys Ile Arg Arg Arg Arg
1               5                   10                  15

Arg Arg Arg Arg
            20

<210> SEQ ID NO 21
<211> LENGTH: 11
<212> TYPE: PRT
<213> ORGANISM: Artificial sequence
<220> FEATURE:
<223> OTHER INFORMATION: Synthetic Polypeptide

<400> SEQUENCE: 21

Ile Thr Cys Val Asp Val Asp Leu Ile Tyr Lys
1               5                   10

<210> SEQ ID NO 22
<211> LENGTH: 9
<212> TYPE: PRT
<213> ORGANISM: Artificial sequence
<220> FEATURE:
<223> OTHER INFORMATION: Synthetic Polypeptide

<400> SEQUENCE: 22

Arg Arg Arg Arg Arg Arg Arg Arg Arg
1               5
```

METHOD AND PEPTIDE FOR REGULATING CELLULAR ACTIVITY

CROSS-REFERENCE TO RELATED APPLICATIONS

This is a continuation of U.S. patent application Ser. No. 12/479,645, filed Jun. 5, 2009 now U.S. Pat. No. 8,071,553, which is a divisional of U.S. patent application Ser. No. 11/656,512, filed Jan. 23, 2007, that issued as U.S. Pat. No. 7,557,086, which is a divisional of U.S. patent application Ser. No. 11/178,316, filed Jul. 12, 2005, that issued as U.S. Pat. No. 7,192,930, which claims priority to U.S. Provisional Application No. 60/586,701, filed Jul. 12, 2004. The prior applications are incorporated by reference herein in their entirety.

STATEMENT REGARDING FEDERALLY SPONSORED RESEARCH OR DEVELOPMENT

The work leading to the present invention was supported by one or more grants from the U.S. Government, including Veterans Affairs RR&D Grant C2870R(SHH), NIH Grant (NIDCD R01 DC05593 (DRT and SHH), and SBIR IR43 DC05882-01 (SEK)). The U.S. Government therefore has certain rights in the invention.

REFERENCE TO SEQUENCE LISTING

The Sequence Listing is submitted as an ASCII text file 6915-81354-03_Sequence_Listing.txt, Oct. 27, 2011, 5.62 KB], which is incorporated by reference herein.

FIELD AND HISTORICAL BACKGROUND OF THE INVENTION

The present invention is generally directed to a method and peptide for regulating cellular activity, and more particularly to the identification and use of various peptides derived from vaccinia virus A52R protein that have biological effects by inhibiting or enhancing cellular activity, and particularly toll-like receptors (TLR) induced cytokine secretion in a cell.

The innate immune system, involved in both the detection and control of infection, recognizes conserved motifs from pathogens termed pathogen-associated molecular patterns (PAMPs) (References 1 and 2). Toll-like receptors (TLRs) recognize PAMPs, and their interaction triggers a series of intracellular signaling events that culminates in expression of cell-surface molecules, secretion of pro-inflammatory cytokines and induction of acquired immunity (References 2-9). TLRs are characterized by an extracellular leucine-rich repeat motif and an intracellular Toll/IL-1 receptor (TIR) domain. Pathogens are detected by the innate immune system, with recognition of the bacterial PAMPs LPS, CpG DNA, flagellin, and peptidoglycan mediated by TLR4, TLR9, TLR5, and TLR2 respectively (References 4 and 10-13). Recognition of viral infections are mediated primarily by TLR3 in response to viral dsRNA (Reference 14). Cell activation in response to different PAMPs involves a number of intracellular molecules common to all TLRs, including MyD88, members of the IL-1 receptor-associated kinase (IRAK) proteins, TNF receptor associated factor (TRAF6), and NF-κB (Reference 1).

Vaccinia virus, a member of the poxvirus family, is a DNA virus that has been demonstrated to encode immunomodulatory proteins (References 15-18). One of these proteins, A52R, has been shown to inhibit NF-κB activation following initiation of the TIR signaling cascade (References 15 and 18). Recent studies have demonstrated that A52R inhibits TIR signaling and contributes to the virulence of vaccinia virus. Inhibition of TIR signaling by A52R is mediated by binding of the protein to both TRAF6 and IRAK2 (Reference 18).

The present invention is directed to the identification and characterization of a peptide, derived from the A52R protein, that significantly inhibits in vitro cytokine production in response to both bacterial and viral PAMPs. This peptide has characteristics consistent with a reagent that inhibits intracellular signaling triggered by TLR activation. Cytokine secretion induced by non-TLR stimulation was not inhibited by the peptide. The in vivo activity of this peptide was demonstrated by dramatically reducing middle ear inflammation in mice injected with heat-inactivated *Streptococcus pneumoniae* (*S. pneumoniae*). This peptide may have application in the treatment of this and other inflammatory conditions that result from ongoing TLR activation. In addition, we have also identified three distinct A52R peptides that inhibit cytokine secretion and five other distinct peptides that enhance cytokine secretion.

OBJECTS AND SUMMARY OF THE INVENTION

The main object of the present invention is to provide a method and peptide for regulating cellular activity.

Another object of the present invention is to provide a peptide for inhibiting cellular activity.

Another object of the present invention is to provide a peptide for enhancing cellular activity.

Another object of the present invention is to provide a peptide that can be used to reduce and/or inhibit pathogen associated inflammation.

Another object of the present invention is to provide a peptide that can be used to reduce and/or inhibit self-antigen associated inflammation.

Another object of the present invention is to provide a peptide that can be used to reduce and/or inhibit antigen associated inflammation.

Another object of the present invention is to provide a peptide that can be used to initiate and/or enhance pathogen associated inflammation.

Another object of the present invention is to provide a peptide that can be used to initiate and/or enhance self-antigen associated inflammation.

Another object of the present invention is to provide a peptide that can be used to initiate and/or enhance antigen associated inflammation.

Another object of the present invention is to provide a peptide that inhibits cytokine secretion in response to TLR activation.

Another object of the present invention is to provide a peptide that inhibits cytokine secretion by interaction with an intracellular portion of the TIR pathway upstream of IkB.

Another object of the present invention is to provide a peptide that inhibits cytokine secretion by interaction in the TIR/TLR signaling pathway.

Another object of the present invention is to provide a peptide that inhibits in vitro cytokine production in response to bacterial and/or viral pathogen-associated molecular patterns (PAMPs).

Another object of the present invention is to provide a peptide that reduces and/or inhibits in vivo inflammation, and particularly bacterial and/or viral-induced inflammation.

Another object of the present invention is to provide a peptide as set forth in SEQ ID NO: 1 to SEQ ID NO: 18, SEQ ID NO: 20, and SEQ ID NO: 21.

Another object of the present invention is to provide a peptide that reduces and/or inhibits fluid secretion and/or accumulation into the middle ear of a subject.

Another object of the present invention is to provide a peptide that reduces and/or inhibits mucosal cellular hypertrophy in the middle ear of a subject.

Another object of the present invention is to provide a peptide that can be used in diagnostic, therapeutic, and/or other applications.

In summary, toll-like receptors recognize and respond to conserved motifs termed pathogen-associated molecular patterns (PAMPs). TLRs are characterized by an extracellular leucine-rich repeat motif and an intracellular Toll/IL-1 receptor (TIR) domain. Triggering of TLRs by PAMPs initiates a series of intracellular signaling events resulting in an inflammatory immune response designed to contain and eliminate the pathogen. Vaccinia virus encodes immunoregulatory proteins, such as A52R, that can effectively inhibit intracellular TIR signaling resulting in a diminished host immune response and enhancing viral survival. The present invention is directed to the identification and characterization of a peptide derived from the A52R protein (sequence DIVKLTVYDCI—SEQ ID NO: 13) that when linked to a 9-arginine cell transduction sequence (SEQ ID NO: 22) effectively inhibits cytokine secretion in response to TLR activation. The peptide had no effect on cytokine secretion resulting from cell activation that was initiated independent of TLR stimulation. Employing a mouse model of otitis media with effusion (OME), administration of heat-inactivated *Streptococcus pneumoniae* (*S. pneumoniae*) into the middle ears of BALB/c mice resulted in a significant inflammatory response that was dramatically reduced with peptide treatment. Experiments have also demonstrated that the peptide will reduce pro-inflammatory mediators in a mouse model of LPS-induced septic shock. The identification of this peptide that selectively targets TLR-dependent signaling may have application in the treatment of chronic inflammation initiated by bacterial or viral infections. In addition to the peptide described above, we have identified three additional distinct peptides from the A52R protein that also inhibit cytokine secretion, and five other distinct peptides that demonstrated enhanced cytokine secretion.

At least one of the above objects is met, in part, by the present invention which in one aspect includes a method of regulating cellular activity, including subjecting a cell to a peptide derived from the vaccinia virus A52R protein.

Another aspect of the present invention includes a method of inhibiting TLR-induced cytokine secretion in a cell, including subjecting a cell to a peptide derived from the vaccinia virus A52R protein.

Another aspect of the present invention includes a method of enhancing TLR-induced cytokine secretion in a cell, including subjecting a cell to a peptide derived from the vaccinia virus A52R protein.

Another aspect of the present invention includes a method of reducing or inhibiting inflammation in a subject, including administering an effective amount of a peptide derived from the vaccinia virus A52R protein in a subject in need thereof.

Another aspect of the present invention includes a method of initiating or enhancing an inflammatory response in a subject, including administering an effective amount of a peptide derived from the vaccinia virus A52R protein in a subject in need thereof.

Another aspect of the present invention includes a synthesized peptide, including at least one amino acid sequence selected from the group consisting of SEQ ID NO: 1 to SEQ ID NO: 18, and a combination thereof.

Another aspect of the present invention includes an immunoregulatory peptide, including at least one amino acid sequence selected from the group consisting of SEQ ID NO: 1 to SEQ ID NO: 18, and a combination thereof.

Another aspect of the present invention includes a fusion peptide, including at least one amino acid sequence selected from the group consisting of SEQ ID NO: 1 to SEQ ID NO: 18, and a combination thereof, and a marker protein and/or a peptide tag.

Another aspect of the present invention includes a complementary peptide for interacting with at least one of the peptides set forth in SEQ ID NO: 1 to SEQ ID NO: 18, and a combination thereof.

Another aspect of the present invention includes an antibody specific for binding to at least one of the peptides set forth in SEQ ID NO: 1 to SEQ ID NO: 18, and a combination thereof.

Another aspect of the present invention includes a pharmaceutical composition including at least one of the peptides set forth in SEQ ID NO: 1 to SEQ ID NO: 18, and a combination thereof.

Another aspect of the present invention includes a synthesized peptide as set forth in SEQ ID NO: 20.

BRIEF DESCRIPTION OF THE DRAWINGS

One of the above and other objects, novel features and advantages of the present invention will become apparent from the following detailed description of the preferred embodiment(s) of the invention, as illustrated in the drawings, in which:

FIG. 1 illustrates internalization of peptide P13 requires the cell transduction sequence: RAW264.7 cells were incubated with 10 μM peptide containing the transducing sequence (DIVKLTVYDCI-RRRRRRRRR; solid line—SEQ ID NO: 20) or with 10 μM peptide lacking the transducing sequence (DIVKLTVYDCI; dashed line—SEQ ID NO: 13) for 15 minutes and internalization of FITC-peptide evaluated by fluorescent-activated cell sorter (FACS);

FIG. 2 illustrates the effect of peptides of the present invention on MIP-2 secretion: RAW264.7 cells were incubated 15 minutes with either medium (no peptide) or individual peptides at the maximal concentrations that did not affect cell viability. The cells were then stimulated with CpG-ODN (1 μg/ml) for 18 hours, cell-free supernatants analyzed for MIP-2 by ELISA, and data expressed as MIP-2 ng/ml+/−S.D.;

FIG. 3 illustrates inhibition of MIP-2 secretion by peptide P13: RAW264.7 cells were incubated 15 minutes with either media (no peptide), 5 μM, 8 μM, or 10 μM peptide P13 and then stimulated with CpG-ODN (1 μg/ml) for 18 hours. Cell-free supernatants were analyzed for MIP-2 by ELISA and data expressed as MIP-2 ng/ml+/−S.D.;

FIG. 4 illustrates inhibition of MIP-2 secretion by peptide P13: RAW264.7 cells were incubated 15 minutes with either media (no peptide), 5 μM, 8 μM, or 10 μM peptide P13 and then stimulated with LPS (1 ng/ml) for 18 hours. Cell-free supernatants were analyzed for MIP-2 by ELISA and data expressed as MIP-2 ng/ml+/−S.D.;

FIG. 5 illustrates inhibition of MIP-2 secretion by peptide P13: RAW264.7 cells were incubated 15 minutes with either media (no peptide), 5 μM, 8 μM, or 10 μM peptide P13 and then stimulated with Poly(I:C) (10 μg/ml) for 18 hours. Cell-free supernatants were analyzed for MIP-2 by ELISA and data expressed as MIP-2 ng/ml+/−S.D., FIG. 6 illustrates inhibition of MIP-2 secretion by peptide P13: RAW264.7 cells were incubated 15 minutes with either media (no peptide), 5 μM, 8 μM, or 10 μM peptide P13 and then stimulated with flagellin (5 ng/ml) for 18 hours. Cell-free supernatants were analyzed for MIP-2 by ELISA and data expressed as MIP-2 ng/ml+/−S.D.;

FIG. 7 illustrates inhibition of MIP-2 secretion by peptide P13: RAW264.7 cells were incubated 15 minutes with either media (no peptide), 5 μM, 8 μM, or 10 μM peptide P13 and then stimulated with zymosan (10 μg/ml) for 18 hours. Cell-free supernatants were analyzed for MIP-2 by ELISA and data expressed as MIP-2 ng/ml+/−S.D.;

FIG. 8 illustrates that peptide P13 inhibits MIP-2 secretion from activated cells: RAW264.7 cells were incubated with peptide P13 for various times; either before (15 minutes), simultaneous with (time 0), or after (0.25, 0.5, 1, 2, 3, or 4 hrs) stimulation for 18 hours with CpG-ODN (1 μg/ml). Positive control was cells stimulated with CpG-ODN (1 μg/ml) without added peptide. Cell-free supernatants were analyzed for MIP-2 by ELISA and data expressed as MIP-2 ng/ml+/−S.D.;

FIG. 9 illustrates peptide P13 inhibition of TNF-α secretion: RAW264.7 cells were incubated for 15 minutes with 10 μM peptide P13 and then stimulated with CpG-ODN (1 μg/ml). Cell-free supernatants were collected after 18 hours and cytokine secretion quantified by ELISA and data expressed as ng/ml+/−S.D.;

FIG. 10 illustrates peptide P13 inhibition of IL-6 secretion: RAW264.7 cells were incubated for 15 minutes with 10 μM peptide P13 and then stimulated with CpG-ODN (1 μg/ml). Cell-free supernatants were collected after 18 hours and cytokine secretion quantified by ELISA and data expressed as ng/ml+/−S.D.;

FIG. 11 illustrates peptide P13 inhibition of IL-10 secretion: RAW264.7 cells were incubated for 15 minutes with 10 μM peptide P13 and then stimulated with CpG-ODN (1 μg/ml). Cell-free supernatants were collected after 18 hours and cytokine secretion quantified by ELISA and data expressed as ng/ml+/−S.D.;

Figure 14:
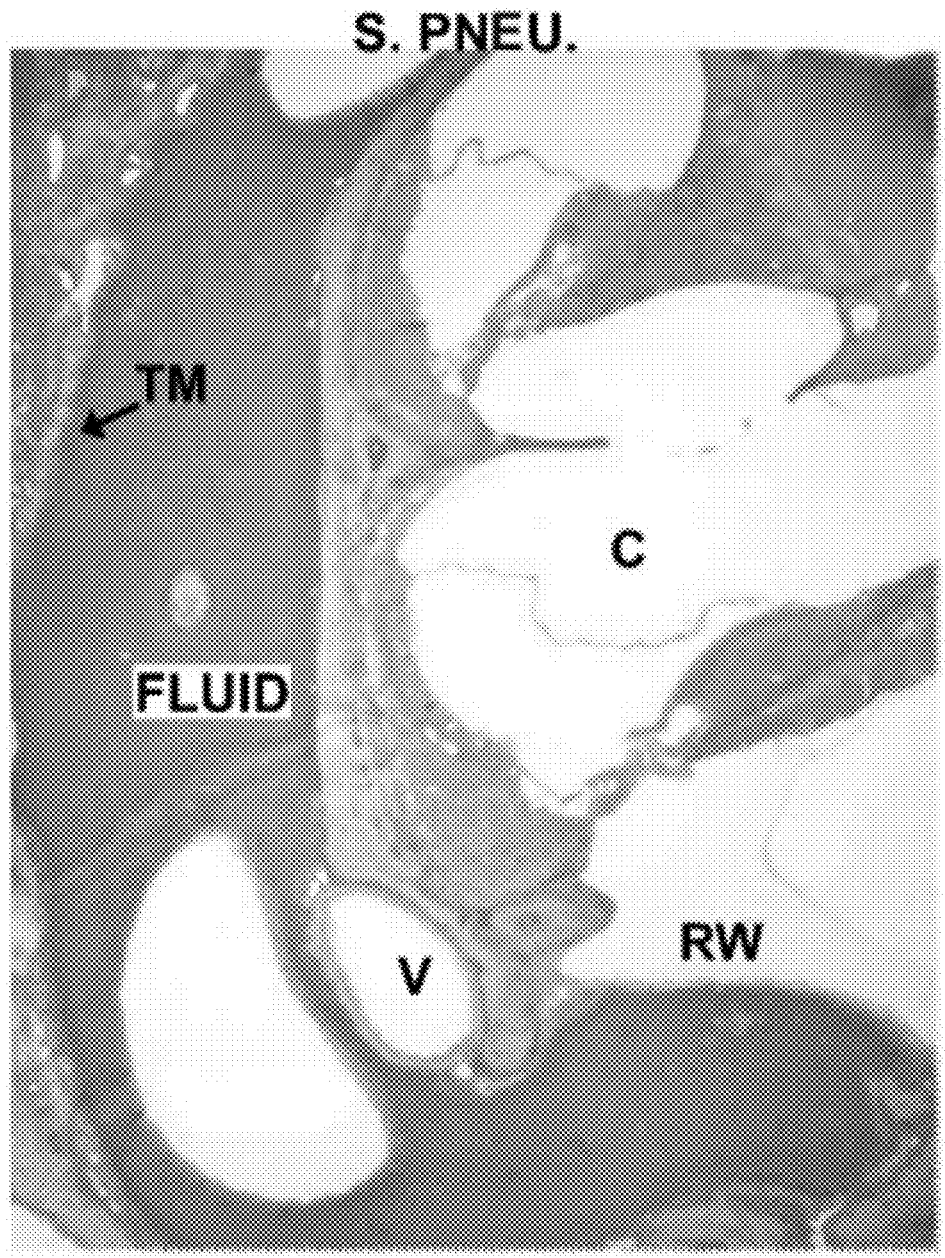
Figure 15:
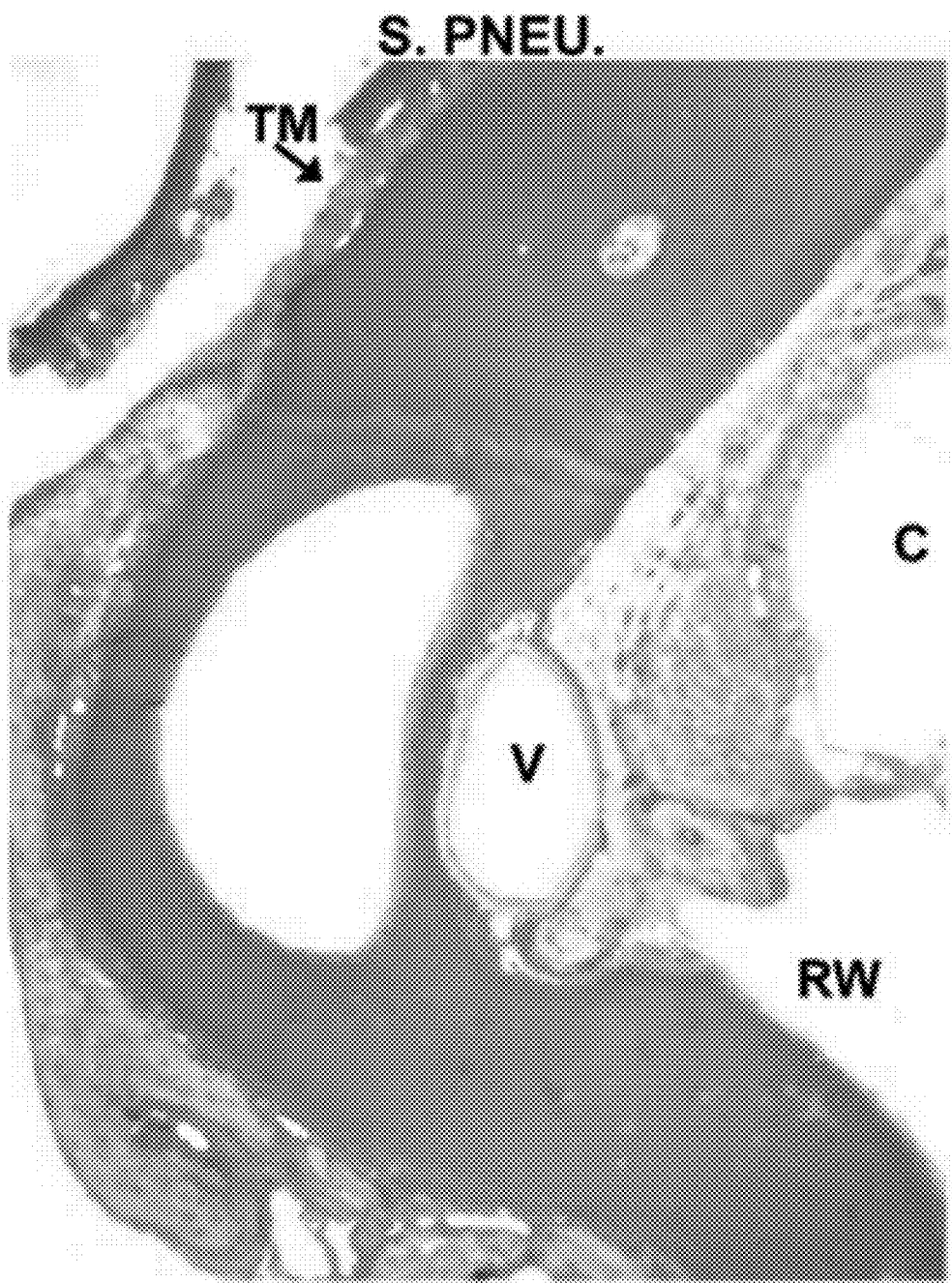
Figure 16:
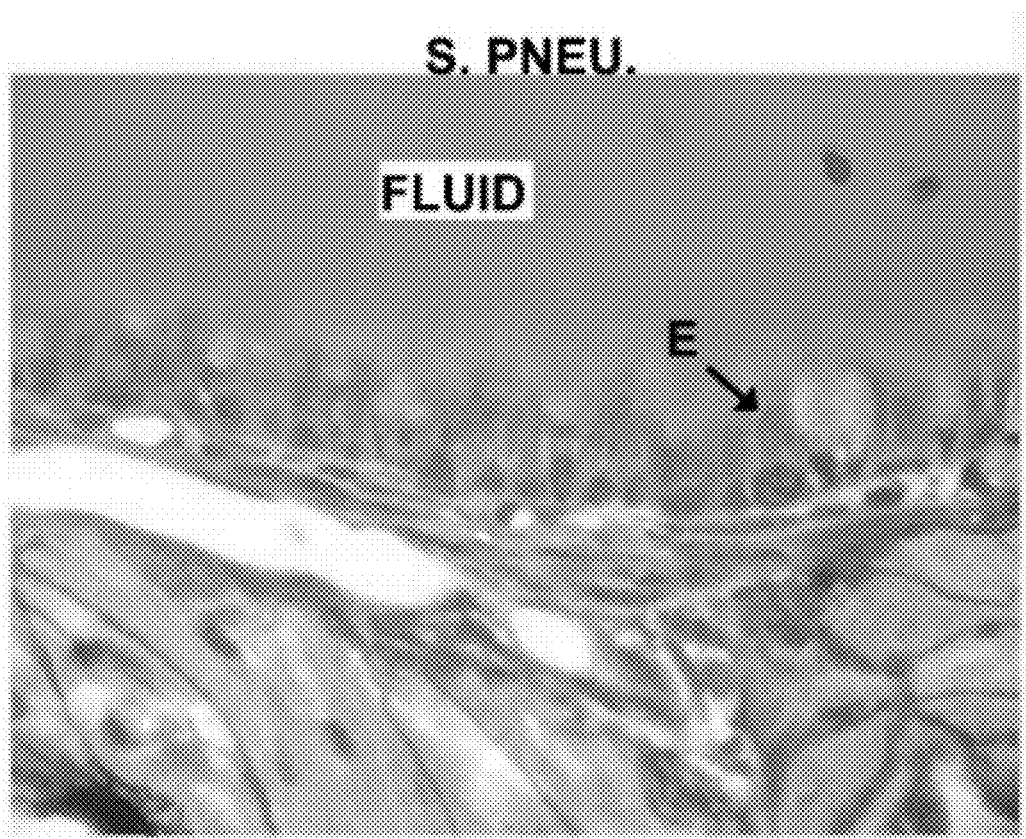
Figure 17:
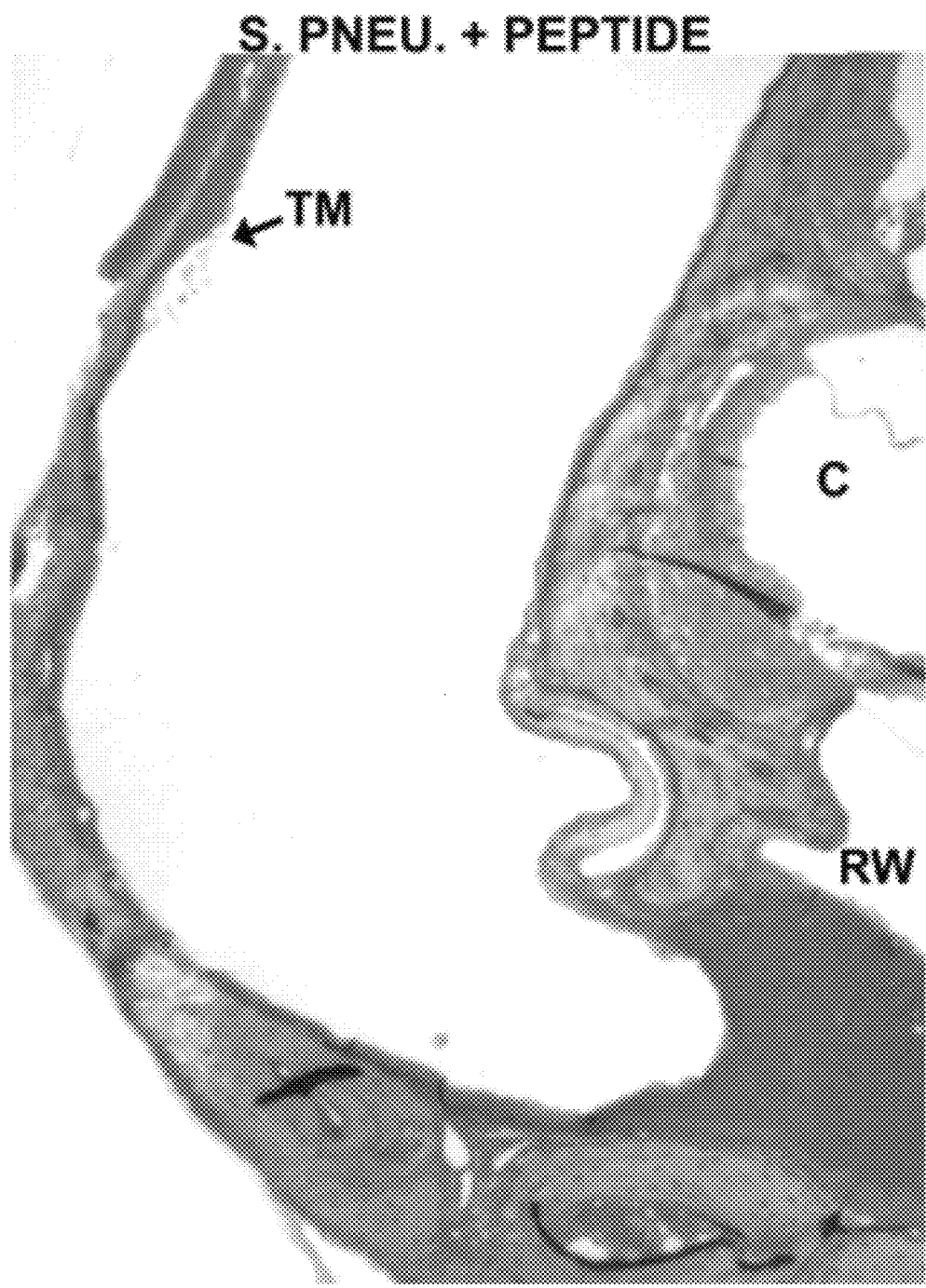
Figure 18:
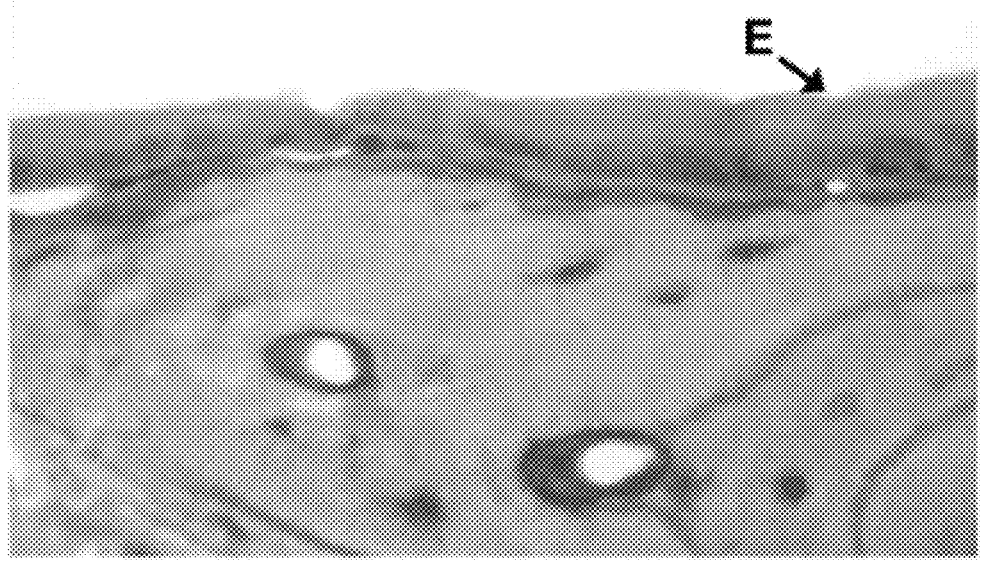
Figure 20:
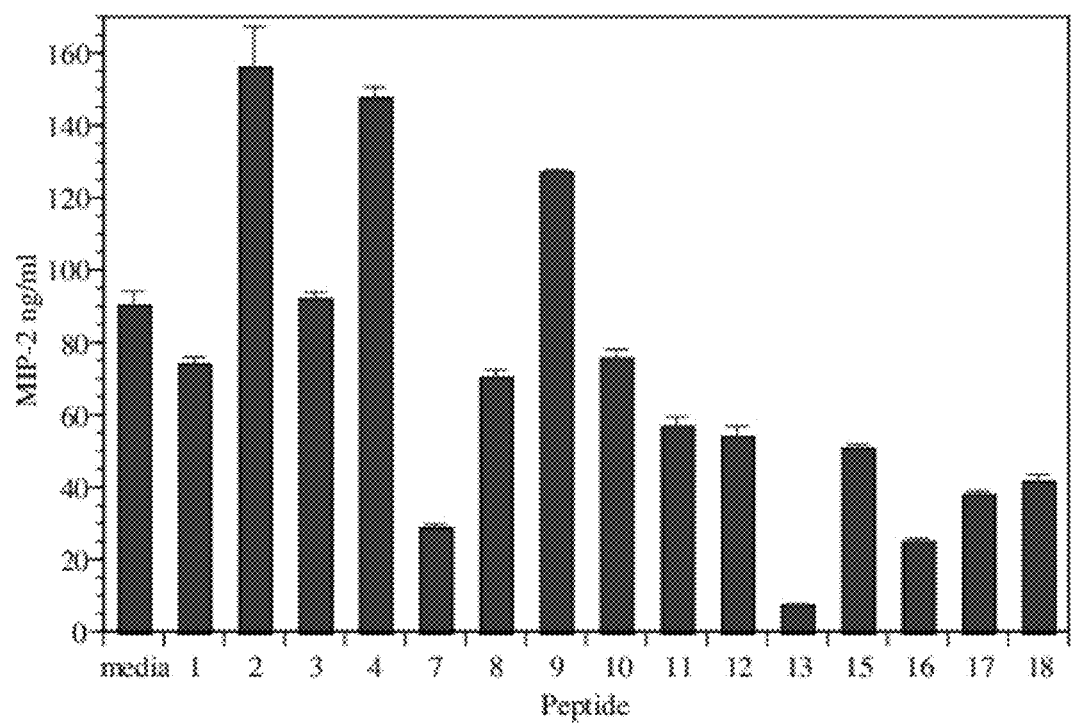
Figure 21:
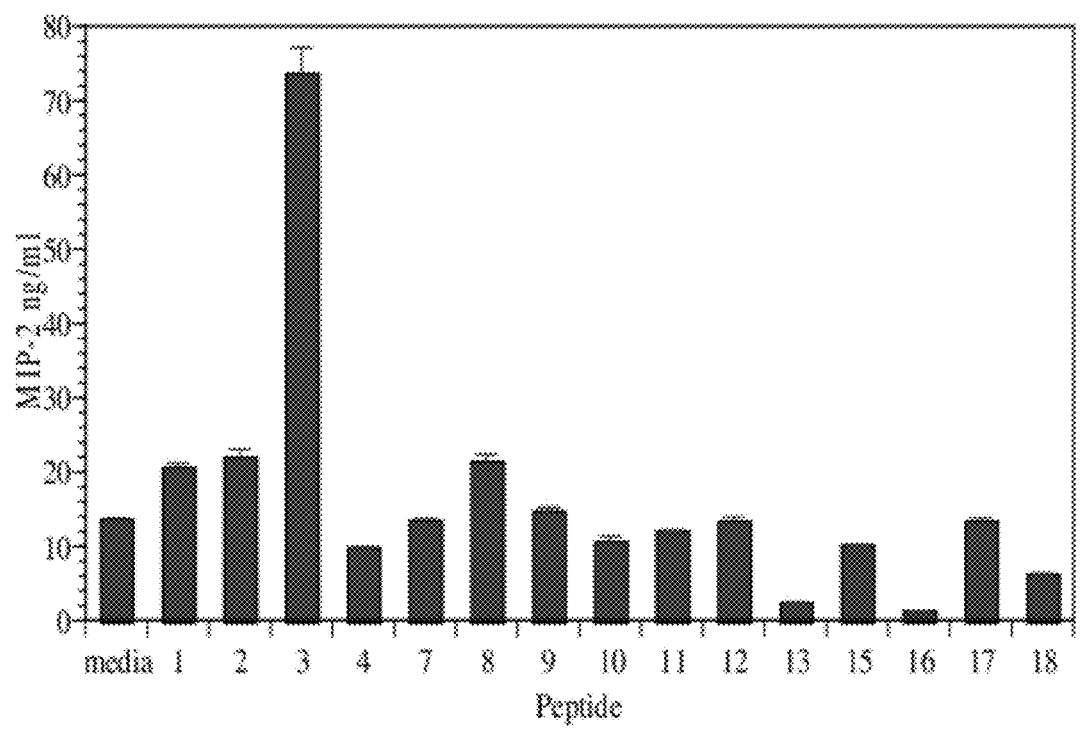

FIG. 14 is a photographic illustration showing that injection of the middle ear with *Streptococcus pneumoniae* (*S. Pneu.*) causes extensive inflammation. The middle ear space lateral to the cochlea (C) and around the stapedial artery (V) is filled with fluid and the tympanic membrane is thickened;

FIG. 15 is a higher magnification photographic illustration of the *S. pneu* injected mouse showing the extensive fluid accumulation in the middle ear space;

FIG. 16 is a photographic illustration showing that *S. pneumoniae* (*S. pneu.*) injection causes hypertrophy of the epithelium, cells become secretory, and fluid accumulates;

FIG. 17 is a photographic illustration showing that the fluid and inflammation is significantly reduced and confined to the round window area when peptide P13 (*S. pneu.*+Pep) is injected with the bacteria;

FIG. 18 is a photographic illustration showing that the epithelium retains a normal appearance and fluid disappears when peptide P13 is injected along with *S. pneumoniae* (*S. pneu.*+Pep);

FIGS. 19A-B illustrate the amino acid sequences (without the nine-arginine cell transducing sequence, SEQ ID NO: 22) of various peptides constructed from the sequence of the vaccinia virus A52R, in accordance with the present invention;

FIG. 20 illustrates the effect of peptides on MIP-2 secretion: RAW264.7 cells were incubated 15 minutes with either medium (no peptide) or individual peptides at the maximal concentrations that did not affect cell viability. The cells were then stimulated with LPS (1 ng/ml) for 18 hours, cell-free supernatants analyzed for MIP-2 by ELISA, and data expressed as MIP-2 ng/ml+/−S.D.;

FIG. 21 illustrates the effect of peptides on MIP-2 secretion: RAW264.7 cells were incubated 15 minutes with either medium (no peptide) or individual peptides at the maximal concentrations that did not affect cell viability. The cells were then stimulated with poly (I:C) (10 μg/ml) for 18 hours, cell-free supernatants analyzed for MIP-2 by ELISA, and data expressed as MIP-2 ng/ml+/−S.D.

DETAILED DESCRIPTION OF THE PREFERRED EMBODIMENT(S) OF THE INVENTION

TLRs are conserved molecular receptors that recognize structures from bacteria, fungi, protozoa, and viruses. Activation of TLRs initiates a series of intracellular events resulting in an innate immune response characterized by the production of pro-inflammatory cytokines (References 2-9). TLR signaling originates from the cytoplasmic TIR domain, conserved among all TLRs. The adapter molecule MyD88, containing both a TIR domain and a death domain, associates with the TIR domain of TLRs and IRAK proteins. Phosporylation of IRAK leads to association with TRAF6 and subsequent activation of NF-κB and secretion of pro-inflammatory cytokines (References 14, 22-25). A52R, an immunoregulatory protein from vaccinia virus, has previously been shown to be an intracellular inhibitor of TIR-dependent signaling (References 15 and 18). When expressed in HEK293 cells, A52R was shown to inhibit NF-κB activation in response to stimulation by a variety of TLRs, including TLR4, TLR5, and the combination of TLR2 and 6, and TLR 2 and 1. In addition, A52R inhibited NF-κB activation in response to Poly (I:C), a synthetic ligand for TLR3. TLR3 has been implicated in an anti-viral innate immune response. The peptide P13 (sequence DIVKLTVYDCI—SEQ ID NO: 13) a subject of the present invention, was derived from the immunoregulatory protein A52R and demonstrates many of the same properties as the protein. The peptide inhibits cytokine secretion in response to a variety of TLR ligands, including LPS (lipopolysaccharide) (TLR4), CpG-ODN (TLR9), Poly (I:C) (TLR3), flaggelin (TLR5), and zymosan (TLR2). Harte and colleagues (Reference 18) have demonstrated that the A52R protein inhibits TIR signaling by binding to both IRAK2 and TRAF6, key intracellular regulatory proteins. These authors further suggest that A52R binds independently to IRAK2 and TRAF6, suggesting the redundant targeting may indicate the importance of inhibiting TIR activation to enhance virulence. Consistent with this speculation, deletion of the A52R protein from vaccinia virus resulted in reduced viral virulence. The mechanism by which peptide P13 inhibits TIR-dependent cytokine secretion remains to be defined. Our studies demonstrated that internalization of the peptide was required for inhibition and that cytokine secretion, in response to non-TLR dependent activation, was not affected. In addition, the demonstration that peptide P13 inhibited phosphorylation of IκB-α and inhibited TLR3 signaling, is consistent with the hypothesis that P13 acts on the TIR signaling pathway at some point between TRAF6 and IκB. Whether peptide P13 associates with TRAF6, like the parent A52R protein, or another intracellular signaling protein further downstream, is currently under investigation.

The in vivo effectiveness of the peptide was demonstrated using a mouse model of OME. OME is an inflammatory disease of the middle ear accompanied by fluid accumulation. It is characterized by an infiltration of leukocytes, macrophages and mast cells and release of inflammatory mediators and enzymes (Reference 21). These mediators increase vascular permeability and secretory activity, and initiate a cascade of inflammatory events, resulting in fluid accumulation and mucin secretion (References 26 and 27). The initiation of inflammation in OME has been attributed to a variety of factors, including bacterial or viral infections, Eustachian tube dysfunction, and allergy. However, the evidence points to a bacterial etiology leading to cytokine activation in the majority of cases. Bacteria have been cultured from up to 40% of effusions and studies have shown bacterial DNA by PCR in approximately 80% of effusions, often in the absence of viable organisms in culture (Reference 28). The most common bacteria invading the middle ear are S. pneumoniae, H. influenzae, and M. catarralis. These three bacteria account for 85% of acute middle ear infections (Reference 27), with S. pneumoniae being the most frequent cause. Initially, live bacteria trigger acute inflammation, which is designed to eliminate the pathogen. During acute infection, interference with the innate immune response would be potentially harmful to the host and may lead to further bacterial spread. Acute inflammation initiated by bacterial infections self-resolves or is treatable by antibiotics. Chronic inflammation involves continued activation of the immune system, often by nonviable bacterial products. OME is often prolonged or antibiotic resistant, suggesting TLR stimulation in absence of live bacteria. We would predict that agents that interfere with TLR-dependent signaling would be potential treatments for prolonged or antibiotic resistant middle ear inflammation. In our studies, treatment of mice with peptide P13 resulted in a significant reduction in bacterial-induced inflammation in the middle ear. Fluid accumulation, infiltrating cells, and tympanic membrane thickness in the middle ear were all dramatically reduced with peptide treatment. Administration of heat-inactivated bacteria, which has a number of potential TLR ligands, induced an inflammatory response in the middle ear most likely resulting from activation of multiple TLRs. In our studies, the use of heat-inactivated bacteria allowed for an examination of peptide inhibition of inflammation without the potential for bacterial spread that may occur in an acute infection initiated with live bacteria. The ability of peptide P13 to significantly inhibit this response in vivo is consistent with the in vitro data showing inhibition of cytokine secretion in response to multiple TLR ligands used either individually or in combination. In these studies a single dose of peptide was administered at the same time as heat-inactivated S. pneumoniae into the middle ears of normal BALB/c mice. While these studies demonstrated a dramatic effect on inflammation, additional studies assessing the effect of peptide treatment on resolving an ongoing inflammatory response are needed. Of interest in this respect, our in vitro data showed inhibition of cytokine secretion even when peptide P13 was added several hours after initiation of TLR activation.

The initiation of an inflammatory response to pathogens is a critical component of the innate immune response and is designed to control infection. However, the sustained production of inflammatory mediators can lead to chronic inflammation, tissue damage and disease development. The signaling cascade initiated by PAMP/TLR interactions and culminating in cell activation has been associated with many disease states, including sepsis, autoimmune diseases, asthma, heart disease and cancer (Reference 29). For example, it is hypothesized that sepsis occurs when bacteria and their products activate an uncontrolled network of host-derived mediators, such as pro-inflammatory cytokines which can lead to multi-organ failure, cardiovascular collapse and death. An abnormal TLR signaling response could lead to exaggerated cell-activation responses contributing to sepsis (Reference 30 and 31). Inflammation is also a key aspect of autoimmunity, and is hypothesized to play a role in tissue destruction in diseases such as multiple sclerosis, rheumatoid arthritis and insulin-dependent diabetes mellitus (Reference 32). Cells of the innate immune system have an essential role in acquired/adaptive immunity. TLR proteins are involved in the maturation and activation of dendritic cells, the antigen-presenting cell type considered most relevant to development of acquired immunity (Reference 33). Allergic asthma is an example of a chronic inflammatory disease with an adaptive immune response, and the TLR signaling pathway is hypothesized to play an important role in the induction phase of an allergic phenotype (Reference 30). Bacterial and viral infections, causing increased inflammatory cell activation, are the main cause of exacerbations in diseases such as asthma and COPD (chronic obstructive pulmonary disease) (Reference 30). Understanding and manipulating the TLR cell activation pathway has the potential to provide therapeutic benefit for a variety of diseases with an inflammatory etiology. Treatments for inflammation have included the use of aspirin and glucocorticoids to block NF-κB activation (References 29, 34, 35) and the targeting of specific inflammatory mediators such as TNF-α (Reference 36). Recent studies report blocking the interaction of TLRs and their ligands (Reference 37), or suppressing TLR expression (References 38-40) may provide new approaches for controlling inflammation. The identification of proteins involved in TIR signaling, and their molecular characterization, have lead to development of agents to inhibit specific points within the TIR signaling cascade. Bartfai and colleagues (Reference 41) have recently reported the synthesis of a low molecular weight mimic of MyD88. The structure of the compound was based on the sequence of the TIR domain. The compound inhibited the interaction between MyD88 and the IL-1R1 TIR domain, thereby inhibiting IL-1 induced activation in vitro and was effective in vivo at blocking IL-1 induced fever in mice. The compound did not block the interaction of TLR4 and MyD88 and therefore LPS induced activation was not inhibited. Inhibition of multiple TLR-dependent responses, by targeting a common signaling component, may prove to be a more effective approach to controlling an inflammatory response.

In the present invention, we identify an 11 amino acid sequence from the vaccinia virus A52R protein that has many of the same immunoregulatory properties described for the whole protein. When linked with a cell transducing sequence, our experiments showed this peptide inhibited in vitro TLR-induced cytokine secretion and in vivo significantly reduced bacterial-induced inflammation in a murine model of OME. In addition, we have identified a panel of other distinct A52R derived peptides that either inhibit or enhance cytokine secretion in response to TLR-dependent stimulation. The treatment and control of bacterial and viral-induced inflammation represents a significant clinical challenge. The selective targeting of the TLR/TIR signaling cascade represents one approach to control inflammation and the identification of these peptides from the A52R protein may have potential therapeutic application.

The peptide 13 sequence was derived from the A52R sequence from vaccinia virus. Blast search analysis shows that peptide P13 has 100% homology with two proteins from vaccinia virus other than A52R, two proteins from cowpox virus, and one protein from rabbit pox virus. Peptide 13 was shown to have significant homology with three separate proteins from three different strains of variola (smallpox) virus: i) A46L from variola major virus strain India ii) A49L from variola minor virus Garcia iii) A44L from variola major virus strain Bangladesh.

Materials and Methods

Peptide synthesis: Peptides were synthesized containing an 11-18 amino acid sequence from the vaccinia virus A52R protein and a 9-residue arginine (SEQ ID NO: 22) cell transduction sequence positioned at the COOH-terminal end to allow for cell internalization. Each peptide was constructed both with and without a FITC-label (Fluorescein isothiocyanate). FITC labeled peptides were used for FACS analysis. The peptides lacking the FITC label were used for in vitro inhibition assays and in vivo treatment studies.

Reagents: Nuclease-resistant phosphorylated oligonucleotide was purchased from Oligos, Inc. (Wilsonville, Oreg.). The sequence was 5'-TCCATGACGTTCCTGACGTT-3' (SEQ ID NO: 19) (CpG ODN) (Reference 19). Mouse IL-1α and TNF-α were purchased from R&D Systems. PMA (phorbol myristate acetate) and LPS (Lipopolysaccaride) were purchased from Sigma. The TLR ligands flagellin, zymosan, and Poly(I:C) were purchased from Invivogen. Cytokine assays were performed using assay kits purchased from R&D Systems. (Heat-inactivated *S. pneumoniae* was the kind gift of Dr. Thomas DeMaria, The Ohio State University College of Medicine, Department of Otolaryngology, Columbus, Ohio.)

Cell lines and Cultures: RAW264.7 (murine monocyte/macrophage) cells (American Type Culture Collection) were cultured at 37° C. in a 5% $CO_2$ humidified incubator and grown in DMEM (Dulbecco's Modified Eagle Medium) (Gibco) supplemented with 10% (v/v) heat-inactivated FCS, 1.5 mM L-glutamine, 100 U/ml penicillin, and 100 μg/ml streptomycin.

Cytokine secretion: RAW264.7 cells were plated at $1.5\times10^5$ cells/well in 48 well plates. After 24 hours, the cells were incubated with peptide at various concentrations at room temperature in triplicate either before, simultaneous with, or after activation with various bacterial or viral PAMPs for 18 hours. Cell-free supernatants were analyzed for cytokines by ELISA, in quadruplicate. RAW264.7 cells were stimulated with either CpG-ODN (1 μg/ml), LPS (1 ng/ml), Poly(I:C) (10 μg/ml), flagellin (5 ng/ml), or zymosan (10 μg/ml). Dose response curves were done with each PAMP to determine optimal stimulation concentration.

Flow Cytometry: Cells were analyzed by flow cytometry (FACScan, Becton Dickinson) using Cellquest software to quantify internalization of peptides. Gates were drawn to exclude dead cells based on 7-AAD (7-amino-actinomycin D) staining. Flourescence due to cell-surface binding of FITC-labeled peptides was quenched using trypan blue. Data obtained were geometric mean fluorescent units (F) with background autofluorescence subtracted.

Immunoblotting: RAW264.7 cells ($6\times10^5$) were plated in 12 well plates overnight. Cells were incubated for 15 minutes at room temperature with either peptide P13 or control scrambled peptide, and then stimulated with medium or LPS (1 ng/ml) for either 15 or 30 minutes. Cells were lysed, and proteins fractionated by SDS/PAGE (Sodium Dodecyl Sulfate/Polyacrylamide Gel Electrophoresis) (12%). Immunoblotting was done using Phospho-IκB-α (Ser32) antibody (Cell Signaling), detected using horseradish peroxidase-conjugated secondary antibody, and visualized by chemiluminescence. Measurements of band intensity were made using the Nucleo Tech Gel Expert software linked to an Epson expression 636 scanner and expressed as intensity/area.

Induction of otitis media: BALB/c (Bagg albino) mice, 8-12 weeks of age, were anesthetized with a subcutaneous injection of xylazine & ketamine (0.1 mg/30 gm body weight) and their ears examined under the operating microscope to assure they were free of infection or perforation. One group of animals (n=5) was injected with PBS (Phospho-buffered saline) in one ear and with 10 μM peptide in the opposite ear, to determine the effect of peptide without added bacteria. A second group of animals (n=20) received 5.0 μl of PBS plus heat-inactivated *S. pneumoniae* ($10^9$ CFU/ml) in one ear and 5.0 μl of peptide (10 μM) plus heat-inactivated *S. pneumoniae* ($10^9$ CFU/ml) in the opposite ear. Injections were done through the tympanic membrane. Animals were killed 3 days after bacterial injection and tissue histologically processed to assess middle ear disease. Inflammation was quantified by measuring 1) area of fluid present in the middle ear, 2) number of cells in middle ear fluid, and 3) thickness of the tympanic membrane (TM) taken at a point away from the injection site. From previous studies, data was obtained from mice (n=18) injected with PBS alone for each of the histological parameters measured, to serve as a control group. Disease induction was defined as positive if the ear injected with *S. pneumoniae* without peptide demonstrated an increase of at least two standard deviations above the control PBS treated mice in at least two of the three parameters assessed for middle ear inflammation: Fluid area, cell number, thickness of the tympanic membrane. Inflammation was successfully induced in 7 of 20 mice.

Tissue Collection: At the end of the experimental treatment, mice were killed and tissues collected for histology. Mice were overdosed on anesthetic and perfused intracardially with 1.0 ml of saline, followed by 20 ml of fixative (1.5% paraformaldehyde-3% glutaraldehyde in 0.1 M phosphate buffer). The middle ears were left intact and connected to each other by the skull base so both ears were processed together for histology and sectioning. This enables all histologic embedding, sectioning, staining, and analysis to be done on the two sides simultaneously to reduce any impact of processing variables on the subsequent quantitative analyses. Middle ears were decalcified, embedded in glycol methacrylate plastic, sectioned at 5 μm, mounted serially on glass slides, stained, and coverslipped.

Histopathologic Analysis: Three consecutive sections at the level of the umbo and promontory were selected for measures of 1) area of fluid present in the middle ear, 2) number of cells in middle ear fluid, and 3) thickness of the tympanic membrane. Each measurement was taken on the three sequential sections per specimen. The value presented for each parameter represents the mean of the three sections.

Statistical analyses: To determine the effect of peptide without added bacteria, animals (n=5) were injected in one ear with PBS alone, and the other ear with 10 μM peptide. Paired t-tests were done comparing the effect of PBS alone with the effect of peptide for each of the 3 histological parameters 1) area of fluid present in the middle ear, 2) number of cells in middle ear fluid, and 3) thickness of the tympanic membrane. Out of 20 animals injected with *S. pneumoniae*, seven met the criteria for disease induction. Paired t-tests were done using these seven animals comparing the effect of peptide plus *S. pneumoniae* in one ear with *S. pneumoniae* alone in the opposite ear for each of the histological parameters described above.

Results

Figure 1:
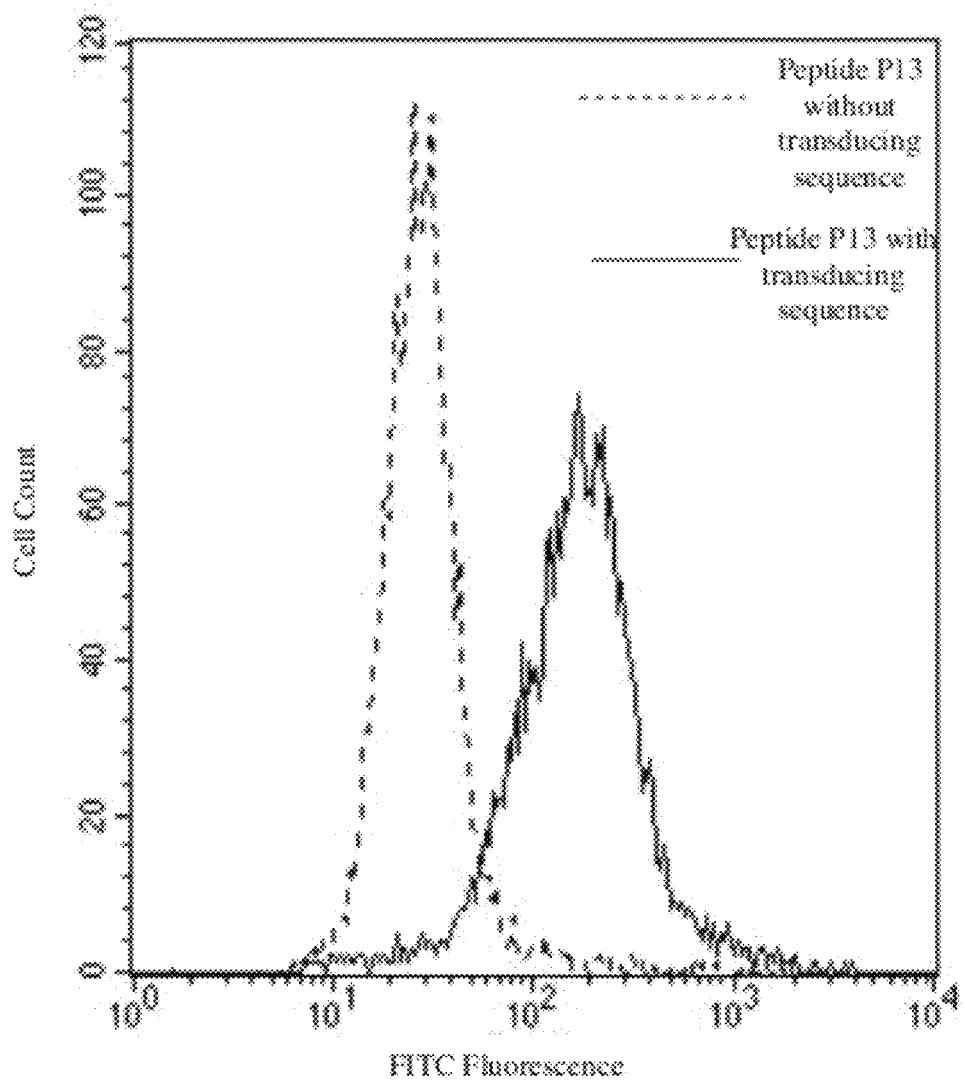
Figure 2:
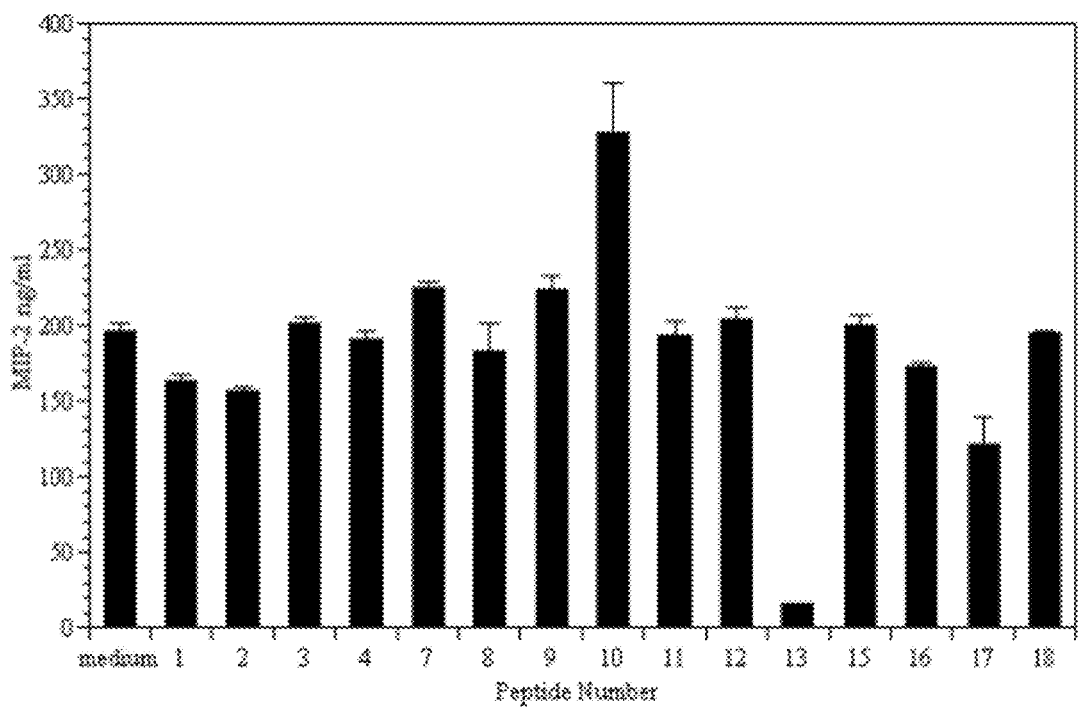
Figure 3:
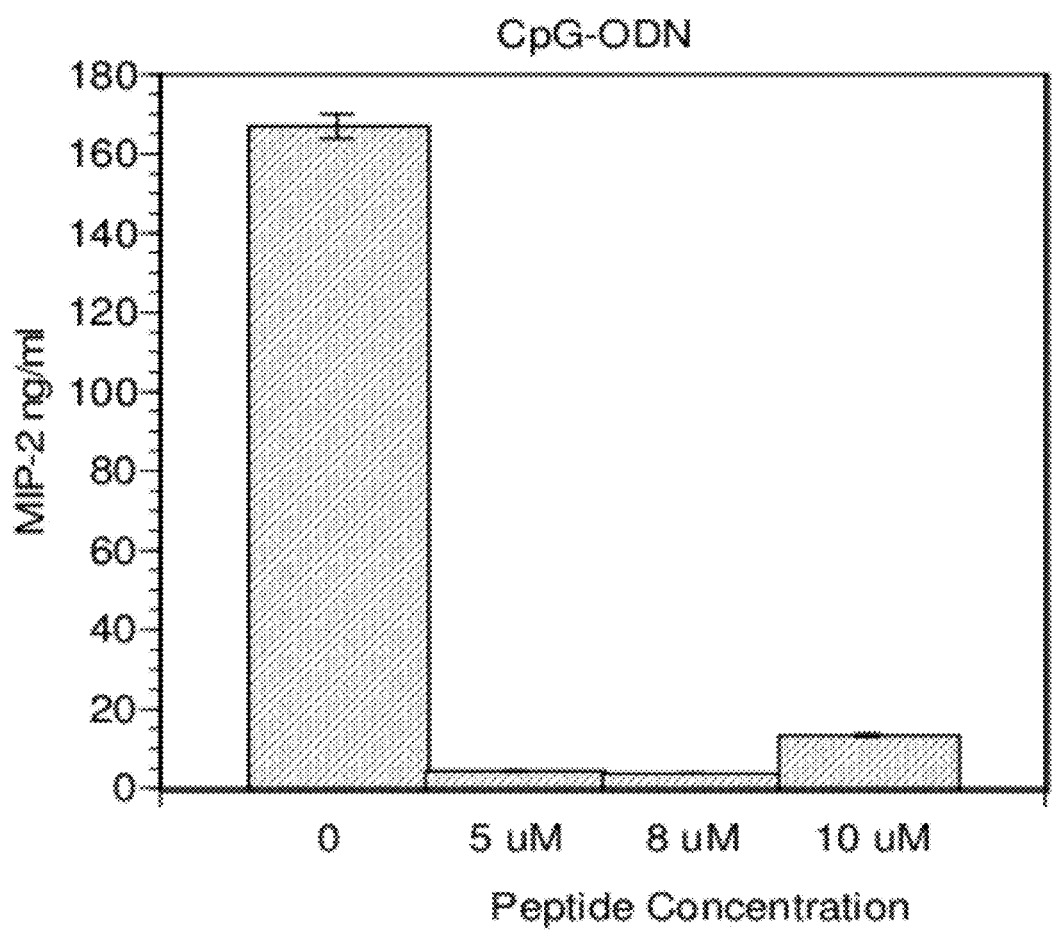
Figure 4:
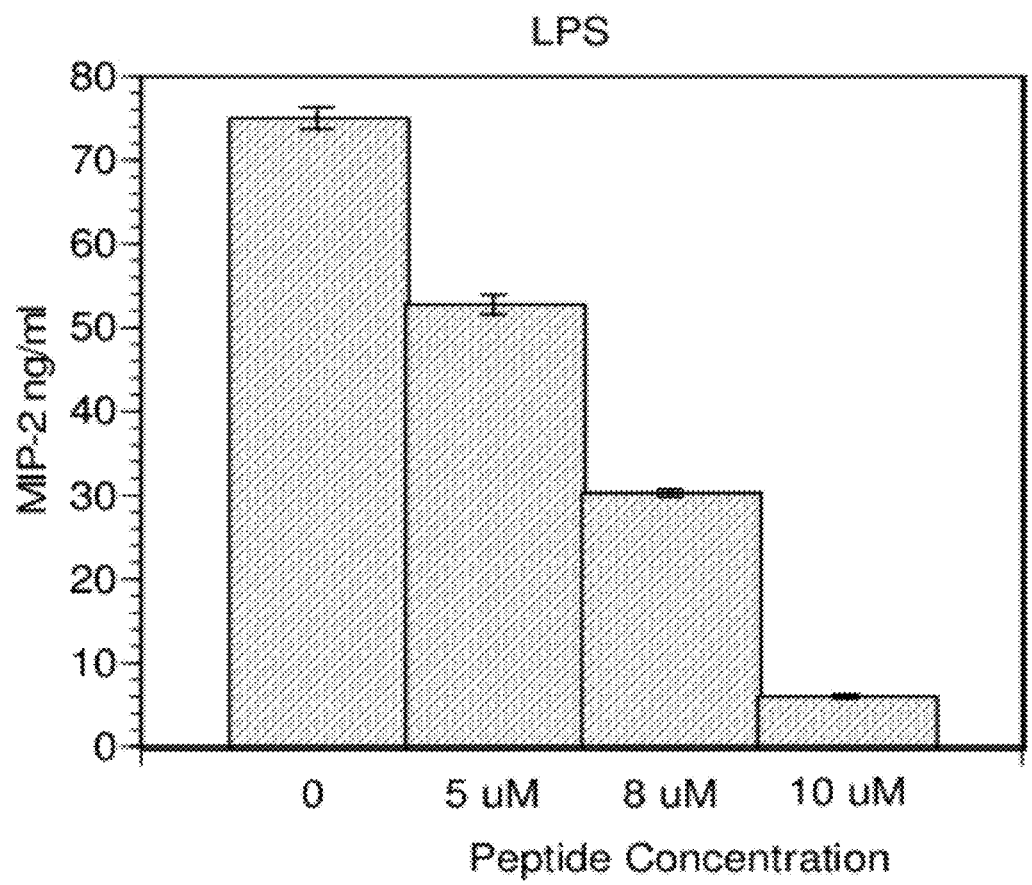

Peptide construction: The A52R protein from vaccinia virus has previously been shown to inhibit intracellular TIR signaling (References 15 and 18). To investigate which amino acid sequence(s) of A52R was responsible for this inhibitory effect, we constructed 18 peptides whose design was based on the sequence of the vaccinia virus A52R protein. Each peptide contained a 9-arginine cell transducing sequence (SEQ ID NO: 22, Reference 20) positioned at the COOH-terminal and an 11-18 amino acid sequence from the vaccinia virus A52R protein. Three peptides (P5, P6, and P14) were found to be insoluble and were eliminated from evaluation. The remaining 15 peptides were evaluated for their effect on cell viability by trypan blue exclusion staining over a range of concentrations and then each peptide was tested for cytokine inhibition at the maximum concentration that had no effect on cell viability. Using the FITC-labeled peptides, each of the peptides was shown to be internalized into RAW264.7 cells, a mouse monocyte/macrophage cell line, as assessed by FACS. The necessity of the cell transducing sequence for cellular internalization was demonstrated when RAW264.7 cells were incubated with one of the FITC-labeled peptides (peptide P13) and internalization assessed by FACS. The amount of FITC-peptide that was internalized into cells produced a geometric mean fluorescent unit (F) value of 151 (FIG. 1). As a control, peptide P13 was produced that contained the 11 amino acid sequence from A52R but lacked the 9-arginine transduction sequence (SEQ ID NO: 22). This FITC-labeled control peptide showed significantly less internalization (F=17) into RAW264.7 cells than the peptide containing the transduction sequence and was similar to the background level seen when cells were incubated with medium without peptide (F=8). In initial experiments, individual peptides (lacking the FITC-label) were examined for inhibition of MIP-2 secretion from RAW264.7 cells. MIP-2 (macrophage inflammatory protein-2), a neutrophil chemoattractant factor, is important in development of inflammation. As a control, each peptide was tested for its effect on cytokine secretion without any added stimulants. These studies demonstrated that all peptides caused <4 ng/ml of MIP-2 secretion in the absence of a stimulus. Individual peptides were then examined for inhibition of MIP-2 secretion from RAW264.7 cells activated by a variety of PAMPs (LPS, Poly (I:C), CpG-ODN). Some peptides demonstrated moderate inhibition of MIP-2 secretion while the majority of peptides examined had no significant effect on cytokine secretion, as demonstrated when cells were stimulated with CpG-ODN (FIG. 2). One peptide (P13), with the amino acid sequence DIVKLTVY-DCI-RRRRRRRRR (SEQ ID NO: 20), demonstrated significant inhibition of MIP-2 secretion for each of the TLR ligands examined and was used for further characterization. A scrambled peptide of P13 (ITCVDVDLIYK-RRRRRRRRR—SEQ ID NO: 21) was also produced as a negative control.

Figure 8:
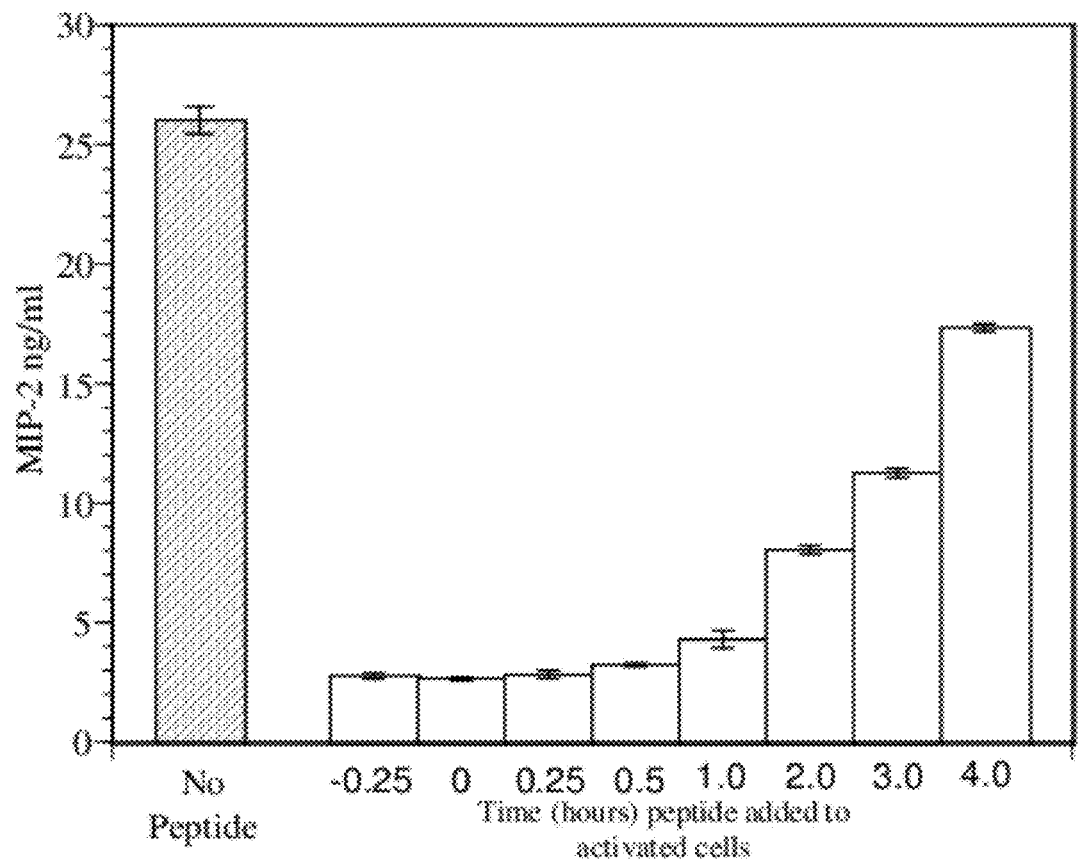
Figure 9:
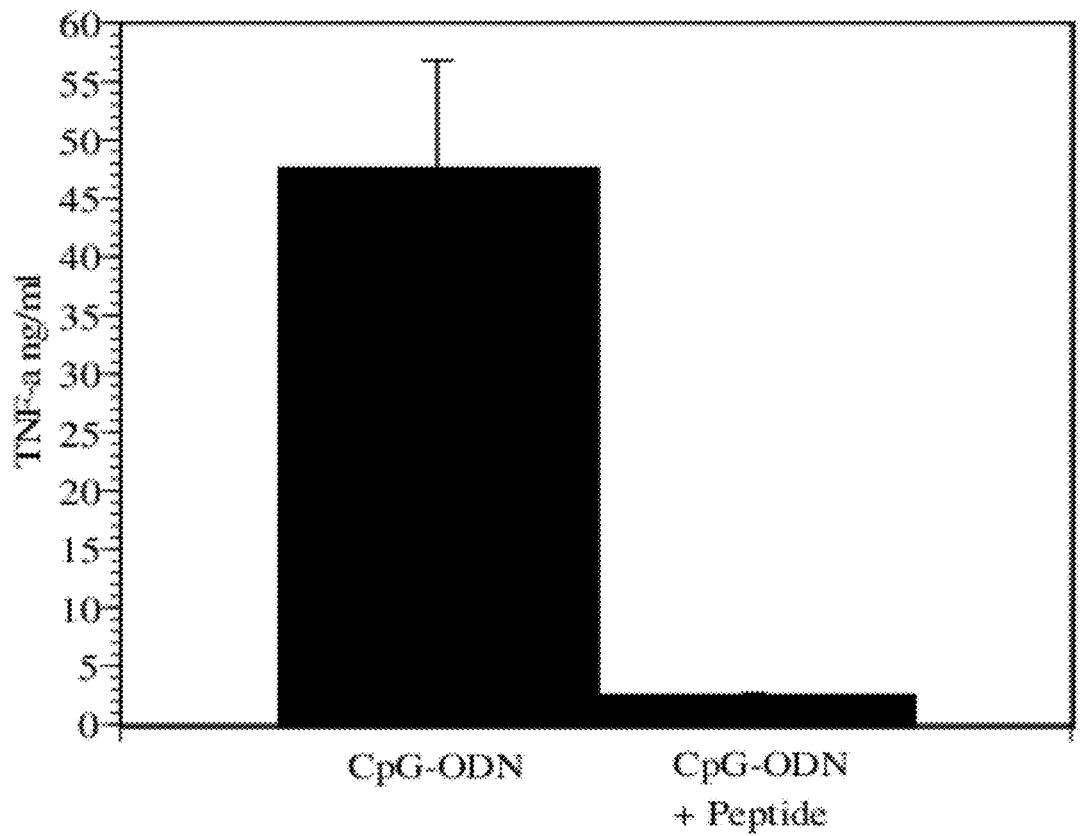
Figure 10:
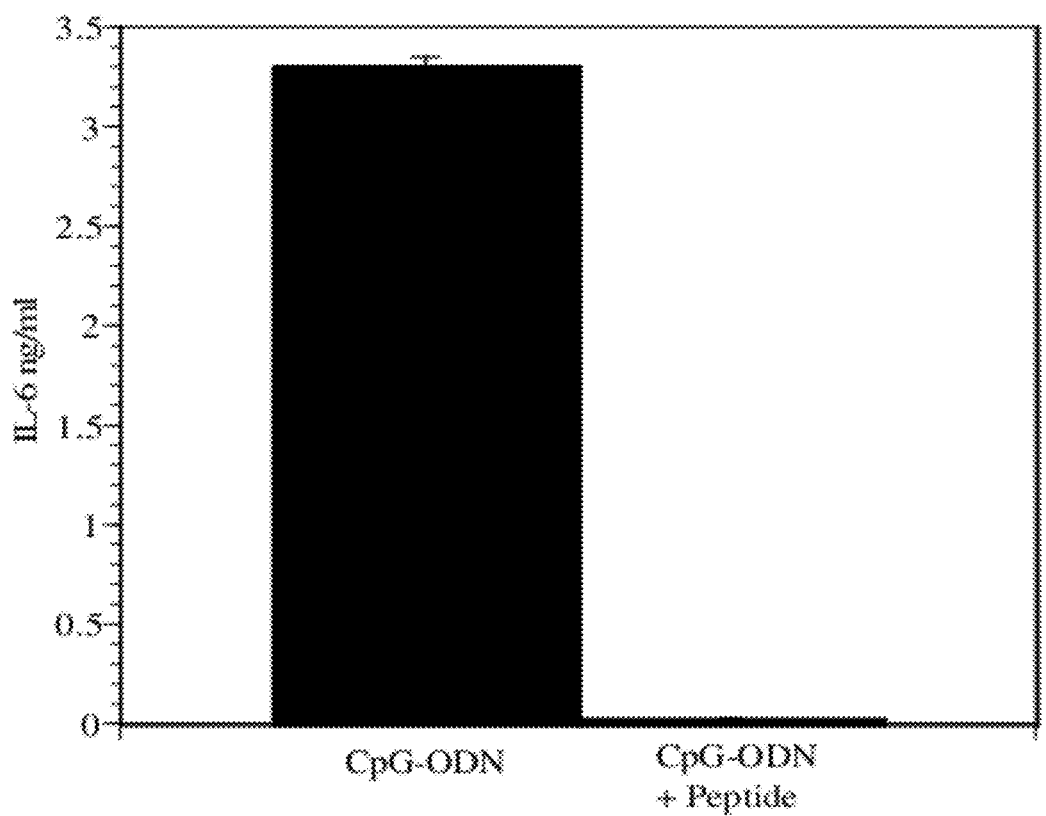
Figure 11:
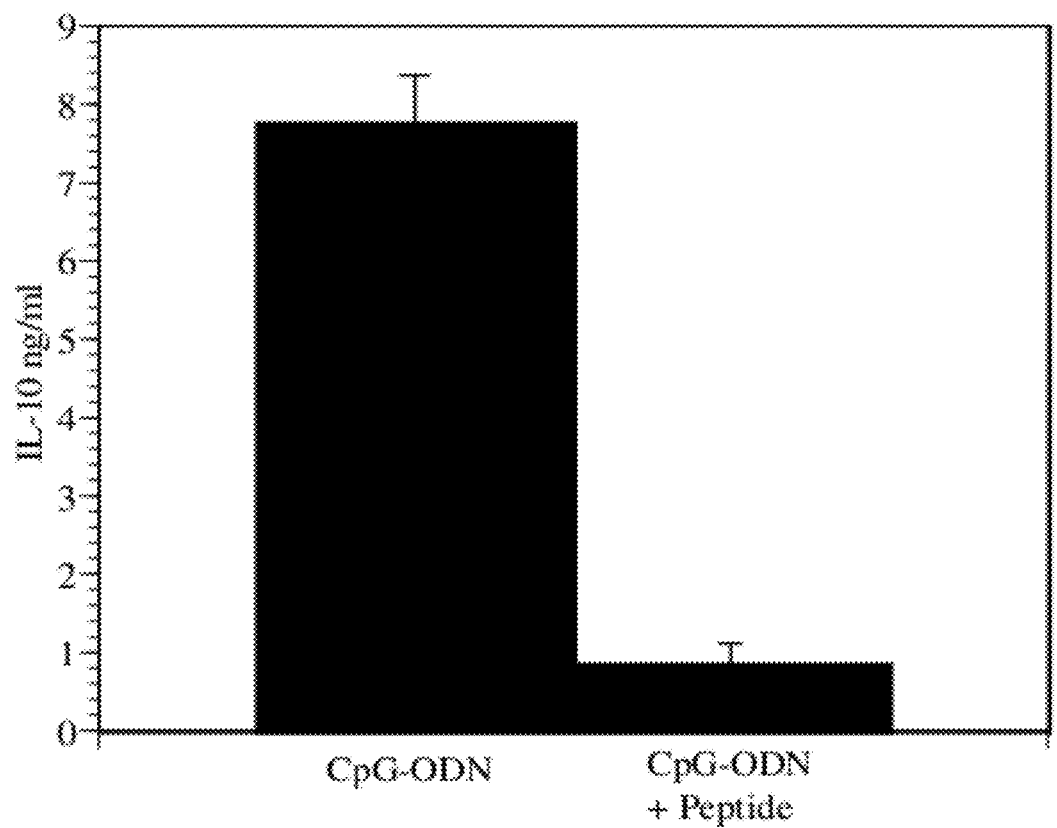

Inhibition of cytokine secretion: The initial studies with peptide P13 examined its effect on MIP-2 secretion at one concentration (10 μM) in response to the stimulants LPS, CpG ODN, and Poly (I:C). Cell viability studies confirmed that a 10 μM concentration of peptides P13 and the scrambled P13 control had no effect on cell viability. Peptide P13 was then examined at various concentrations for inhibition of cytokine secretion in response to these and other TLR ligands. RAW264.7 cells were incubated for 15 minutes with 5, 8, or 10 μM of peptide P13 and then stimulated with either CpG-ODN, LPS, Poly (I:C), flagellin, or zymosan for 18 hours. Cell-free supernatants from treated cells were assessed for MIP-2 by ELISA. Treatment with peptide significantly inhibited MIP-2 secretion for each of the 5 TLR ligands examined (FIGS. 3-7). Peptide inhibition of MIP-2 secretion was dose-dependent for the TLR ligands LPS, Poly (I:C), and flagellin. Inhibition was most dramatic when cells were stimulated with CpG ODN, and ranged from approximately 90% to 35%, depending upon the TLR ligand used for cell activation. Testing of the control scrambled peptide at 10 μM, under identical experimental conditions, showed no inhibition of MIP-2 secretion in response to the five PAMPs examined above. To determine if peptide P13 would be effective in inhibiting cytokine secretion induced by a combination of stimuli, RAW264.7 cells were incubated with both LPS (0.5 ng/ml) and CpG-ODN (0.5 ug/ml). Each stimulus was used at half of its optimal stimulatory concentration. Incubation with 10 μM peptide P13 reduced MIP-2 secretion 81%. We next sought to establish the effect on MIP-2 secretion when peptide was added at various time points before, simultaneous with, or after stimulation with CpG-ODN. Inhibition seen after addition of peptide P13 up to one hour after stimulation with CpG-ODN was similar to inhibition seen when peptide was added either before or simultaneous with CpG-ODN (>85% inhibition). Significant inhibition of MIP-2 secretion was demonstrated even when peptide was added as long as 4 hours after stimulation of cells with CpG-ODN (FIG. 8). Peptide inhibition of cytokines other than MIP-2 was also examined. RAW264.7 cells were stimulated with CpG-ODN and secretion of TNF-α, IL-6, and IL-10 quantified by ELISA. Treatment of cells with peptide P13 significantly inhibited secretion of each of these cytokines (FIGS. 9-11). In addition, peptide inhibited intracellular TNF-α production by 59% as assessed by FACS. Inhibition of cytokine secretion by peptide P13 was also seen when human BJAB B cells were activated by TLR ligands. In summary, the peptide demonstrated inhibition of cytokines stimulated by numerous TLR ligands, both alone and in combination. The inhibition was dose-dependent and seen for a variety of cytokines produced by both macrophages and B cells. Peptide P13 was effective even when added after the stimulating PAMP, suggesting a potential application as an anti-inflammatory therapy.

Figure 5:
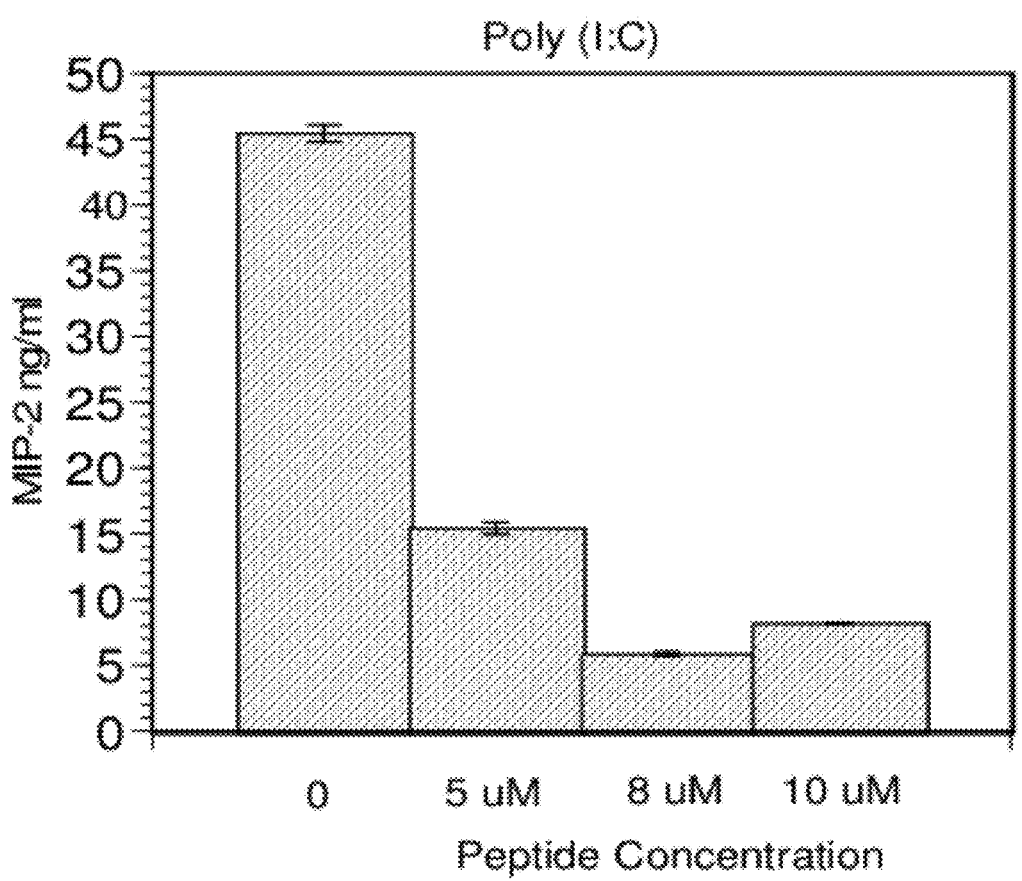
Figure 6:
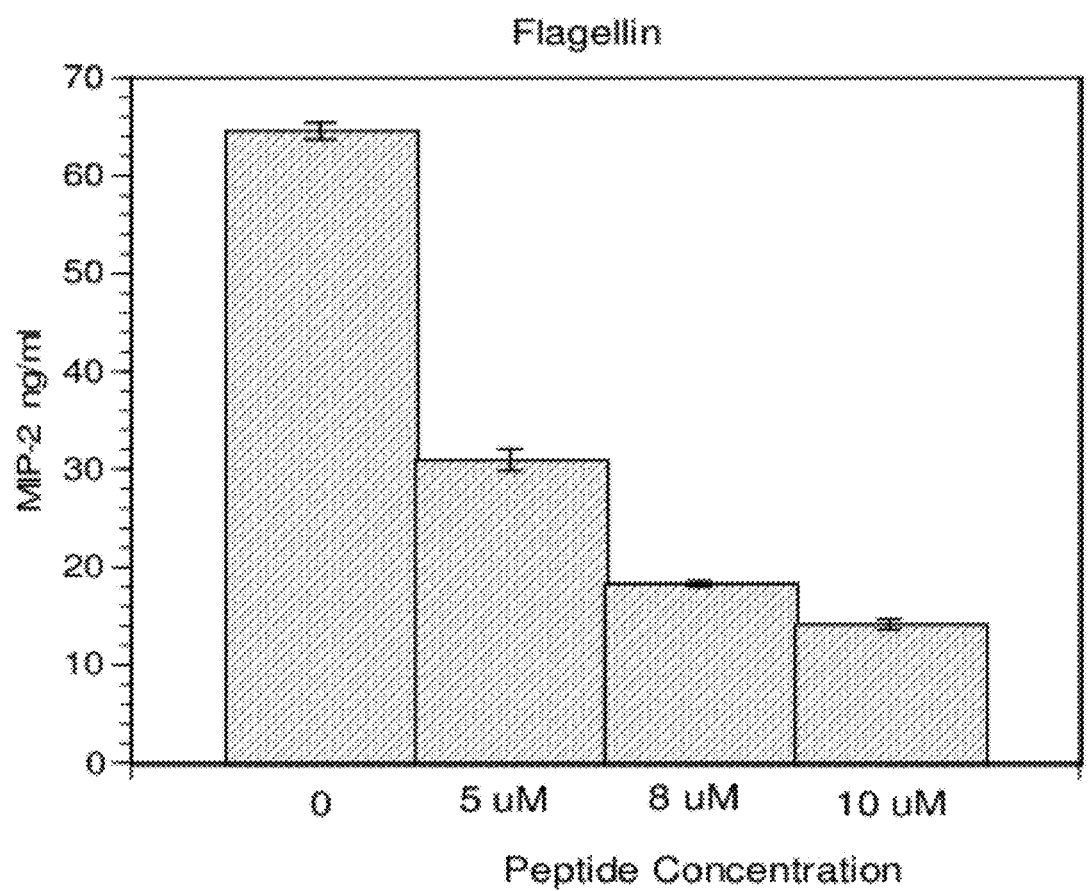
Figure 7:
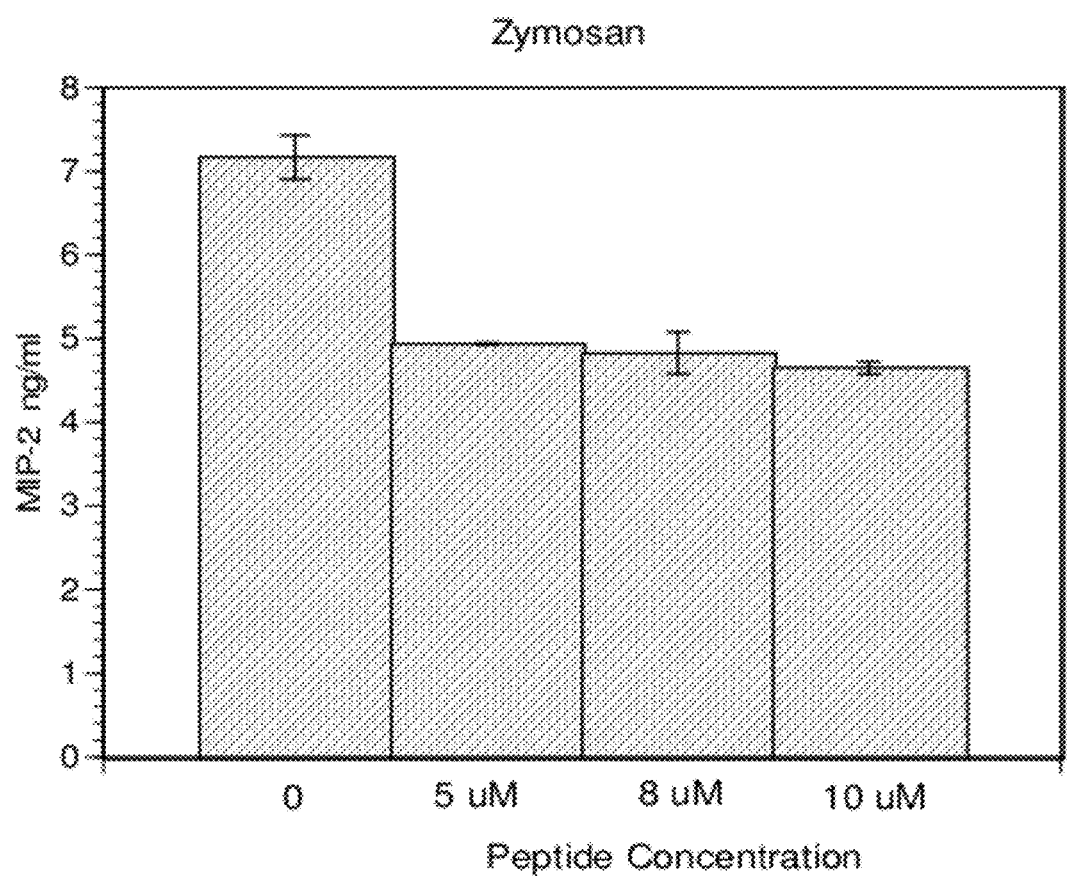

Mechanism of peptide P13 inhibition of cytokine secretion: The A52R protein has been previously demonstrated to inhibit TIR signaling by interacting with both IRAK2 (interleukin-1 receptor-associated kinase 2) and TRAF6 (TNF (tumor necrosis factor) receptor associated factor 6), intracellular signaling molecules involved in TIR signaling (Reference 18). We hypothesize that P13, like the parent protein, inhibits cytokine secretion through interaction with IRAK2 and/or TRAF6. Data from the following experiments support this hypothesis. i) Peptide P13 must be internalized to inhibit cytokine secretion. To interact with IRAK2 and/or TRAF6, peptide P13 must be internalized. We compared treatment of cells with peptide P13 that either contained or lacked the 9-arginine cell transducing sequence (SEQ ID NO: 22). Peptide without the transducing sequence was not internalized into cells as previously demonstrated (FIG. 1). Treatment of RAW264.7 cells with peptide P13 lacking the transducing sequence had no effect on MIP-2 secretion in response to stimulation with either LPS or CpG-ODN (Table I). As previously demonstrated, peptide containing the cell transducing sequence significantly inhibited MIP-2 secretion (FIGS. 3-7). ii) Peptide P13 does not inhibit cytokine secretion stimulated by PMA or TNF-α. Both PMA and TNF-α activate RAW264.7 cells via signaling pathways independent of either IRAK2 or TRAF6, resulting in secretion of MIP-2. Treatment with peptide had no affect on MIP-2 secretion in response to stimulation with either PMA or TNF-α (Table II).

iii) Peptide P13 inhibits phosphorylation of IκB-α. The intracellular signaling pathway triggered by the interaction of PAMPs with TLRs involves the IRAK (interleukin-1 receptor-associated kinase) family and TRAF6, resulting in translocation of NF-κB to the nucleus, followed by secretion of pro-inflammatory cytokines. Activation of NF-κB is dependent on the phosphorylation and proteolysis of the IκB proteins. RAW264.7 cells were treated with either peptide P13 or control scrambled peptide and stimulated with LPS for either 15 or 30 minutes. Cells were lysed and analyzed by immunblotting using Phospho-IκB-α antibody, which detects endogenous levels of IκB-α only when phosporylated at Ser32. Peptide P13 completely inhibited the phosphorylation of IκB-α in LPS activated cells as compared to cells treated with control scrambled peptide, which demonstrated a two-fold increase overbackground (Table III). iv) Peptide P13 inhibits cytokine secretion initiated by TLR3. The TLR3 signaling pathway is different from the other TLR signaling pathways in that it requires TRAF6, but not the IRAK family or the upstream adaptor molecule MyD88, for the production of pro-inflammatory cytokines. Downstream of TRAF6, the pathways are similar, both resulting in the phosphorylation of IκB and the translocation of NF-κB to the nucleus. As demonstrated above, peptide P13 inhibits MIP-2 production from RAW264.7 cells stimulated with Poly(I:C), a synthetic ligand for TLR3 (FIG. 5). Collectively, these data support the conclusion that peptide P13 inhibits cytokine secretion by interaction with an intracellular portion of the TIR signaling pathway upstream of IκB. The inhibition of TLR3 mediated cytokine secretion, in combination with the other PAMP/TLR inhibitory data, suggests that the effect of peptide P13 is on TRAF6 or a downstream component of the TIR signaling pathway. The data are consistent with the hypothesis that peptide P13, like the parent A52R protein, interacts in the TIR signaling pathway at TRAF6.

Figure 12:
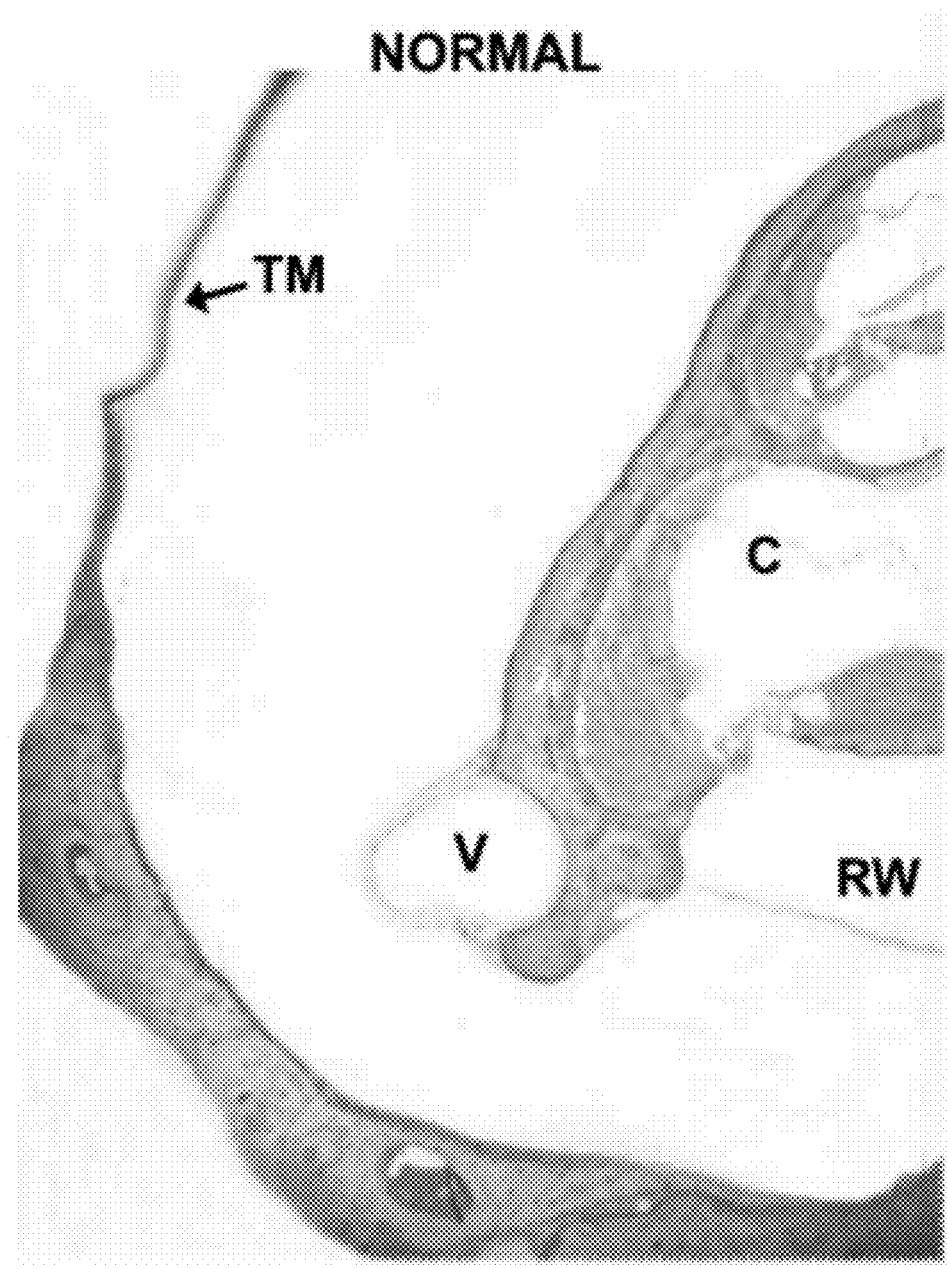
FIG. 12 is a photographic illustration of the middle ear from after treatment with peptide P13 The normal middle ear of BALB/c mice is clear between the tympanic membrane (TM) and round window (RW)
Figure 13:
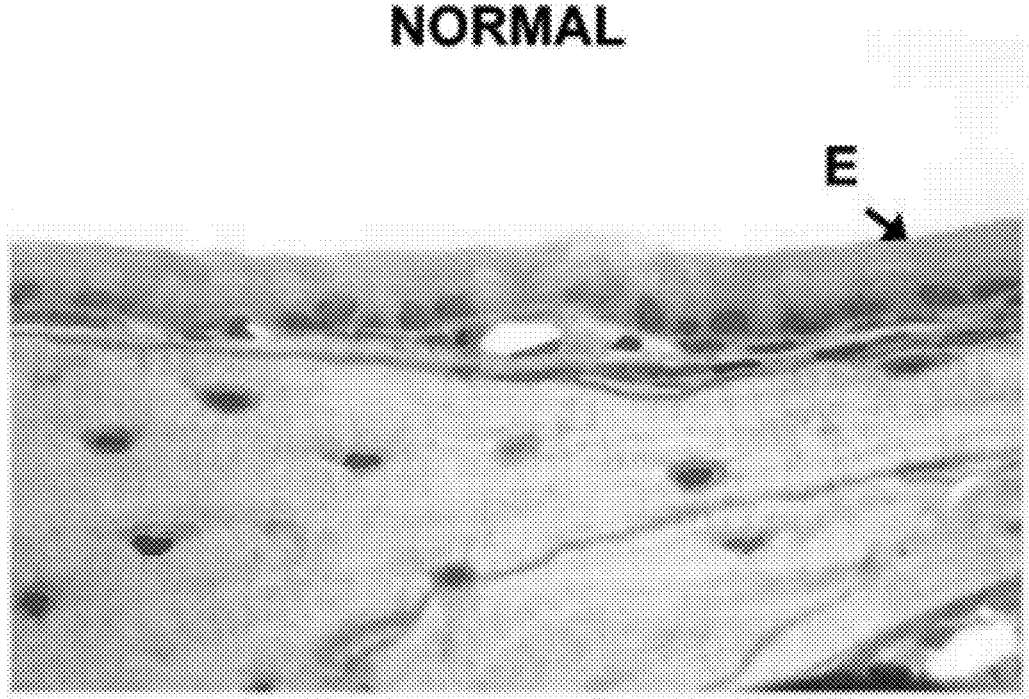
FIG. 13 is a photographic illustration of the mucosal epithelium after treatment with peptide P13. The normal mucosal epithelium (E) of the middle ear lateral wall is typically comprised of only 1-2 layers of low cuboidal cells.

Inhibition of middle ear inflammation: The effect of peptide P13 on bacterial-induced inflammation in vivo was examined using a murine model of otitis media with effusion (OME). The inflammatory response in bacterial-induced OME is initiated by TLR activation and is characterized by infiltration of cells into the middle ear, fluid accumulation, and thickening of the mucosal epithelium and the tympanic membrane (Reference 21). To first examine any potential effects caused by peptide alone without added bacteria, five mice were injected in one ear with PBS and in the opposite ear with 10 μM peptide P13. Three days later the animals were killed, middle ears embedded, sectioned, stained and evaluated for fluid area, infiltrating cell number, and thickness of the tympanic membrane. Paired t-tests (2-tailed) were used to analyze each of the three parameters. In the absence of bacterial-induced inflammation, no differences were seen between the PBS injected ear and peptide P13 injected ear in i) fluid area (p=0.104), ii) cell number (p=0.880), or iii) tympanic membrane thickness (p=0.891). To examine the effectiveness of the peptide to affect inflammation in vivo, twenty BALB/c mice were injected in the middle ear on one side with heat-inactivated S. pneumoniae plus PBS and in the middle ear on the opposite side with heat-inactivated S. pneumoniae plus 10 μM peptide P13. Three days later the animals were killed, and evaluated for middle ear fluid area, infiltrating cell number, and thickness of the tympanic membrane. Disease development was defined as an increase over background controls (PBS injected ears n=18) of at least two standard deviations in two out of the three parameters quantified. A total of 7 out of 20 mice met the criteria for disease induction. Analysis of middle ears by paired t-tests from these 7 mice with disease showed that peptide treatment significantly reduced the amount of fluid (p=0.004), infiltrating cell number (p=0.02), and thickness of the tympanic membrane (p=0.002), all parameters of middle ear inflammation (Table IV). Examination of these three parameters of inflammation for each individual mouse with disease illustrates the dramatic effect seen with a single treatment of peptide P13 (Table V). Of interest, 6 out of the 7 mice demonstrated reductions in all areas of inflammation, while one animal (#4-182) showed only modest reduction in fluid area and tympanic membrane thickness, and no reduction in cell number. Photographs from a normal, non-diseased animal and a representative animal with disease illustrate the effect of peptide on bacterial-induced inflammation in vivo. The middle ear of normal mice is free of fluid or cells (FIG. 12) and the mucosal epithelium that lines the middle ear space is normally comprised of 1-2 low cuboidal cells (FIG. 13). Injection of heat-killed bacteria resulted in a marked inflammatory response in the middle ear after 3 days. This was characterized by mucosal and tympanic membrane swelling, cellular infiltration, and significant fluid (effusion) secretion and accumulation that filled the middle ear space (FIGS. 14 and 15). The inflammatory response led to significant mucosal cellular hypertrophy and active secretion of mucins and other fluids (FIG. 16). When peptide P13 was injected with the bacteria, a significant reduction was seen in fluid accumulation into the middle ear space (FIG. 17) and reduced mucosal hypertrophy (FIG. 18).

Inhibition of inflammatory mediators in a murine septic shock model: Preliminary data has been collected documenting the inhibitory effect of peptide P13 on inflammatory mediators in a murine septic shock model. BALB/c mice (4 animals/group) were injected i.p. with PBS, LPS at 100 μg/mouse/250 μl, or 100 μg LPS plus various doses of peptide P13. Serum was collected at 2 and 6 hours after treatment and evaluated for the pro-inflammatory cytokines MIP-2 and TNF-α by ELISA, and for soluable ICAM-1. The animals injected simultaneously with peptide P13 and 100 μg LPS showed up to a 31% reduction in MIP-2, a 60% reduction in TNF-α, and a 35% reduction in soluable ICAM-1 as compared to animals injected only with LPS.

Other immunomodulatory peptides derived from A52R: Eighteen peptides were designed and constructed based on the sequence of the vaccinia virus A52R protein as described previously in this manuscript. Each peptide contained a nine-arginine cell transducing sequence (SEQ ID NO: 22) positioned at the C terminus and an 11- to 18-aa sequence from the vaccinia virus A52R protein (FIG. 19). Three peptides (P5, P6, and P14) were found to be insoluble and were eliminated from evaluation. Each of the remaining 15 peptides were examined for inhibition of MIP-2 secretion from RAW264.7 cells activated by the PAMPs LPS, poly(I:C) and CpG-ODN. Peptide P13 was found to have the greatest inhibitory activity and was used for further characterization as previously described. Several other peptides were also identified for further study, based either on the peptide's inhibitory activity, or on the ability of the peptide to enhance cytokine production. Using the data generated by stimulation with CpG-ODN, P13 was selected for its ability to inhibit cytokine activity, and P10 for its cytokine enhancing ability (FIG. 2). Cellular stimulation with LPS (FIG. 20) yielded three peptides that significantly enhanced MIP-2 production, (P2, P4, P9), and three that inhibited cytokine activity (P7, P13, P16). Data from cell stimulated with poly(I:C) showed four peptides of interest, P3, which increases MIP-2 production, and P13, P16 and P18, which show inhibitory activity (FIG. 21). In summary, we have demonstrated that peptide P13 (FIG. 22) is a potent inhibitor of cytokine secretion and bacterial-induced inflammation. In addition to peptide P13, we demonstrated that peptides P7, P16 and P18 (FIG. 22) also inhibited cytokine activity. Peptides P2, P3, P4, P9 and P10 (FIG. 23) demonstrated enhanced cytokine activity.

TABLE I

Peptide P13 Lacking a Cell Transducing Sequence Fails to Inhibit MIP-2 Secretion

| Treatment | MIP-2 (pg/ml +/− S.D.)[a] | % Inhibition |
|---|---|---|
| LPS | 46,618 +/− 923 | |
| LPS + peptide P13 | 12,435 +/− 269 | 73% |
| LPS + peptide P13 (no transducing sequence) | 46,931 +/− 1335 | 0% |
| CpG-ODN | 31,194 +/− 743 | |
| CpG-ODN + peptide P13 | 3242 +/− 238 | 90% |
| CpG-ODN + peptide P13 (no transducing sequence) | 29,312 +/− 618 | 6% |

[a]RAW264.7 cells were incubated 15 minutes with either medium, peptide P13 containing the transducing sequence, or peptide P13 lacking the transducing sequence and then stimulated with either LPS (1 ng/ml) or CpG ODN (1 µg/ml). Cell-free supernatants were analyzed for MIP-2 by ELISA and data expressed as pg/ml +/− S.D.

TABLE II

Peptide P13 Does Not Inhibit Non-TLR Induced MIP-2 Secretion

| Treatment[a] | MIP-2 pg/ml (+/−S.D.) |
|---|---|
| Medium | 781 +/− 7 |
| TNF-α | 1744 +/− 16 |
| TNF-α + peptide P13 | 2384 +/− 16 |
| PMA | 22,144 +/− 544 |
| PMA + peptide P13 | 24,736 +/− 1216 |

[a] RAW264.7 cells were incubated 15 minutes with either medium or peptide P13 and then stimulated with either medium, TNF-α (100 ng/ml) or PMA (100 ng/ml) for 18 hours. Cell-free supernatants were analyzed for MIP-2 by ELISA and data expressed as pg/ml +/− S.D.

TABLE III

Peptide P13 Inhibits Phosphorylation of IκB-α

| | Phosphorylated IκB-α Band Intensity/Area[a] | |
|---|---|---|
| Treatment | Scrambled peptide | Peptide P13 |
| medium | 6.3 | 5.4 |
| LPS (15 min) | 13.1 | 4.9 |
| LPS (30 min) | 13.3 | 3.1 |

[a]RAW264.7 cells were incubated 15 minutes with either peptide P13 or control scrambled peptide and then treated with either medium, or LPS (1 ng/ml) for either 15 or 30 minutes. Immunoblotting was performed using phospo-IκB-α (ser32) antibody. Measurements of band intensity were made using the Nucleo Tech Gel Expert Software linked to an Epson expression 636 scanner and data expressed as band intensity/area.

TABLE IV

Peptide P13 Inhibition of Middle Ear Inflammation[a]

| Treatment | Fluid Area (microns +/− S.D.) | Cell Number (+/−S.D.) | Tympanic Membrane Thickness (microns +/− S.D.) |
|---|---|---|---|
| PBS[b] | 1016 +/− 1397 | 31 +/− 41 | 44 +/− 20 |
| S. pneumoniae[c] | 5771 +/− 2077 | 252 +/− 140 | 105 +/− 33 |
| S. pneumoniae + peptide P13[c] | 1486 +/− 1192 | 111 +/− 119 | 44 +/− 15 |
| p value (2-tailed)[d] | p = 0.004 | p = 0.020 | p = 0.002 |

[a] Middle ear inflammation was assessed by measuring three consecutive tissue sections for area of fluid in the middle ear, number of cells in the middle ear fluid, and thickness of the tympanic membrane measured at a point away from the injection site. Data represent the mean +/− SD of 7 animals with middle ear inflammation. Statistical evaluation was done using a paired t-test.
[b] The PBS treated animals (n = 18) received no bacteria or peptide P13.
[c] Animals (n = 7) injected in one ear with S. pneumoniae plus PBS and in the opposite ear injected with S. pneumoniae plus peptide P13 (10 µM).
[d] Statistical evaluation using a paired t-test was done using data collected from diseased animals (n = 7) injected with bacteria and comparing peptide vs. no peptide P13 treatment.

TABLE V

Peptide P13 Inhibits Development of Fluid, Cell Number, and Tympanic Membrane Thickening in a Murine Model of OME[a]

| Animal | Fluid Area % inhibition | Cell Number % inhibition | Tympanic membrane thickness % inhibition |
|---|---|---|---|
| #4-21 | 84% | 39% | 63% |
| #4-24 | 85% | 96% | 65% |
| #4-177 | 86% | 77% | 66% |
| #4-182 | 11% | 0 | 22% |
| #4-183 | 73% | 44% | 71% |
| #4-185 | 66% | 77% | 60% |
| #4-195 | 94% | 89% | 69% |

[a] Middle ear inflammation was assessed as described in Table III. Percent inhibition is calculated by comparing fluid area, cell number, and tympanic membrane thickness seen in one ear injected with S. pneumoniae plus PBS with the same parameters of inflammation seen in the opposite ear injected with S. pneumoniae plus peptide P13 (10 µM).

While this invention has been described as having preferred sequences, ranges, steps, materials, structures, features, and/or designs, it is understood that it is capable of further modifications, uses and/or adaptations of the invention following in general the principle of the invention, and including such departures from the present disclosure as those come within the known or customary practice in the art to which the invention pertains, and as may be applied to the central features hereinbefore set forth, and fall within the scope of the invention and of the limits of the appended claims.

REFERENCES

The following references, and those cited in the disclosure herein, are hereby incorporated herein in their entirety by reference.
1. Takeda, K., and S. Akira 2004. TLR signaling pathways. *Seminars in Immunology* 16:3.
2. Schnare M., G. M. Barton, A. C. Holt, K. Takeda, S. Akira, and R. Medzhitov. 2001. Toll-like receptor control activation of adaptive immune responses. *Nat. Immuno.* 2:947.
3. Granucci, F., C. Vizzardelli, N. Pavelka, S. Feau, M. Persico, E. Virzi, M. Rescigno, G. Moro, and P. Ricciardi-Castagnoli. 2001. Inducible Il-2 production by dendritic cells revealed by global gene expression analysis. *Nat. Immunol.* 2:882.
4. Krieg, A. M. 2002. CpG motifs in bacterial DNA and their immune effects. *Ann. Rev. Immunol.* 20:709.
5. Trinchieri, G. 1998. Interleukin-12: a cytokine at the interface of inflammation and immunity. *Adv. Immunol.* 70:83.

6. Ozato, K., H. Tsujimura, and T Tamura. 2002. Toll-like receptor signaling and regulation of cytokine gene expression in the immune system. *BioTechniques Oct. Suppl:*66.
7. Yi, A. K., J. G. Yoon, S. J. Yeo, S. C. Hong, B. K. English, and A. M. Krieg. 2002. Role of mitogen-activated protein kinases in CpG DNA-mediated IL-10 and IL-12 production: central role of extracellular signal-regulated kinase in the negative feedback loop of the CpG DNA-mediated Th1 response. *J. Immunol.* 168:4711.
8. Fan, J. and A. B. Malik. 2003. Toll-like receptor-4(TLR4) signaling augments chemokine-induced neutrophil migration by modulating cell surface expression of chemokine receptors. *Nat. Med.* 9:315.
9. McCoy, S. L., S. E. Kurtz, F. A. Hausman, S. R. Trune, R. M. Bennett, and S. H. Hefeneider. 2004. Activation of RAW264.7 macrophages by bacterial DNA and lipopolysaccharide increases cell surface DNA binding and internalization. *J. Biol. Chem.* 279:17217.
10. Hoshino, K., O. Takeuchi, T. Kawai, H. Sanjo, T. Ogawa, Y. Takeda, K. Takeda, and S. Akira 1999. Cutting Edge: Toll-like receptor 4 (TLR4)-deficient mice are hyporesponsive to lipopolysaccharide: evidence for TLR4 as the Lps gene product. *J. Immunol.* 162:3749.
11. Hemmi, H., O. Takeuchi, T. Kawai, T. Kaisho, S. Sato, H. Sanjo, M. Matsumo, K. Hoshino, H. Wagner, K. Takeda, and S. Akira 2000. A Toll-like receptor recognizes bacterial DNA. *Nature* 408:740.
12. Hayashi, F., K. D. Smith, A. Ozinsky, T. R. Hawn, E. C.Yi, D. R. Goodlett, J. K. Eng, S. Akira, D, M. Underhill, and A. Aderem. 2001. The innate immune response to bacterial flagellin is mediated by Toll-like receptor 5. *Nature* 410:1099.
13. Takeda, K., T. Kaisho, and S. Akira 2003. Toll-like receptors. *Ann. Rev. Immunol.* 21:335.
14. Akira, S. 2003. Mammalian Toll-like receptors. *Curr. Opin. Immunol.* 15:5.
15. Bowie, A., E. Kiss-Toth, J. A. Symons, G. L. Smith, S. K. Dower, and L. A. J. O'Neill. 2000. A46R and A52R from vaccinia virus are antagonists of host IL-1 and toll-like receptor signaling. *Proc. Natl. Acad. Sci. U.S.A.* 97:10162.
16. O'Neill L. 2000. The Toll/interleukin-1 receptor domain: a molecular switch for inflammation and host defence. *Biochem. Soc. Trans.* 28:557.
17. Bellows, C. F., R. F. Garry, and B. M. Jaffe. 2003. Vaccinia virus-induced inhibition of nitric oxide production. *J. Surg. Res.* 111:127.
18. Harte, M. T., I. R. Haga, G. Maloney, P. Gray, P. C. Reading, N. W. Bartlett, G. L. Smith, A. Bowie, and L. A. J. O'Neill. 2003. The poxvirus protein A52R targets Toll-like receptor signaling complexes to suppress host defense. *J. Exp. Med.* 197:343.
19. Yi, A. K., and A. M. Krieg. 1998. Cutting Edge: Rapid induction of mitogen-activated protein kinases by immune stimulatory CpG DNA. *J. Immunol.* 161:4493.
20. Wender, P. A., D. J. Mitchell, K. Pattabiraman, E. T. Pelkey, and L. Steinman. 2000. The design, synthesis, and evaluation of molecules that enable or enhance cellular uptake: Peptoid molecular transporters. *Proc. Natl. Acad. Sci. U.S.A.* 97:13003.
21. Barzilai A., B. Dekel, R. Dagan, and E. Leibovitz. 2000. Middle ear effusion Il-6 concentration in bacterial and non-bacterial acute otitis media. *Acta Paediatr* 89:1068.
22. Takeda, K. and S. Akira 2004. TLR signaling pathways. *Semin. Immunol.* 16:3.
23. Janssens, S., and R. Beyaert. 2003. Functional diversity and regulation of different interleukin-1 receptor-associated kinase (IRAK) family members. *Mol. Cell* 11:293.
24. Daun, J. M., and M. J. Fenton. 2000. Interleukin-1/Toll receptor family members: receptor structure and signal transduction pathways. *J. Interferon Cytokine Res.* 20:843.
25. Barton, G. M., and R. Medzhitov. 2003. Linking Toll-like receptors to IFN-α/β expression. *Nat. Immunol.* 4:432.
26. Karasen R. M.,Y. Sutbeyaz, B. Aktan, H. Ozdemir, and C. Gundogu. 2000. Effect of web 2170 BS, platelet activating factor receptor inhibitor, in the guinea pig model of middle ear inflammation. *Ann Otol Rhinol Laryngol* 109:549.
27. Daly, K. A., L. L. Hunter, and G. S. Giebink. 1999. Chronic Otitis Media with Effusion. *Pediatrics in Review* 20:85.
28. Kubba H., J. P. Pearson, and J. P. Birchall. 2000. The aetiology of otitis media with effusion: a review. *Clin Otolaryngol* 25:181.
29. O'Neill, L. A. J. 2003. Therapeutic targeting of Toll-like receptors for inflammatory and infectious diseases. *Curr. Opin. Pharm.* 3:396.
30. Zuany-Amorim, C., J. Hastewell, and C. Walker. 2002. Toll-like receptors as potential therapeutic targets for multiple diseases. *Nat. Rev. Drug Discov.* 1:797.
31. Ikezoe, T., Y. Yang, D. Heber, H. Taguchi, and H. P. Koeffler. 2003. PC-SPES: A potent inhibitor of nuclear factor-κB rescues mice from lipopolysaccharide-induced septic shock. *Mol. Pharmacol.* 64:1521.
32. Delgado, M., C. Abad, C. Martinez, M. G. Juarranz, J. Leceta, D. Ganea, and R. P. Gomariz. 2003. PACAP in immunity and inflammation. *Ann. N. Y. Acad. Sci.* 992:141.
33. Basu, S., and M. J. Fenton. 2004. Toll-like receptors: function and roles in lung disease. *Am. J. Physiol. Lung Cell Mol. Physiol.* 286:L887.
34. Kopp, E., and S. Ghosh. 1994. Inhibition of NF-kappa B by sodium salicylate and aspirin. *Science* 265:956.
35. Almawi, W. Y., and O. K. Melemedjian. 2002. Negative regulation of nuclear factor-kappaB activation and function by glucocorticoids. *J. Mol. Endocrinol.* 28:69.
36. Andreakos, E. T., B. M. Foxwell, F. M. Brennan, R. N. Maini, and M. Feldmann. 2002. Cytokines and anti-cytokine biologicals in autoimmunity: present and future. *Cytokine Growth Factor Rev.* 13:299.
37. Meng, G., M. Rutz, M. Schiemann, J. Metzger, A. Grabiec, R. Schwandner, P. B. Luppa, F. Ebel, D. H. Busch, S. Bauer, H. Wagner, and C. J. Kirschning. 2004. Antagonistic antibody prevents Toll-like receptor 2-driven lethal shock-like syndromes. *J. Clin. Invest.* 113:1473.
38. Sweet, M. J., B. P. Leung, D. Kang, M. Sogaard, K. Schulz, V. Trajkovic, C. C. Campbell, D. Xu, and F. Y. Liew. 2001. A novel pathway regulating lipopolysaccharide-induced shock by ST2/T1 via inhibition of Toll-like receptor 4 expression. *J. Immunol.* 166:6633.
39. Brint, E. K., D. Xu, H. Liu, A. Dunne, A. N. McKenzie, L. A. O'Neill, and F. Y. Liew. 2004. ST2 is an inhibitor of interleukin 1 receptor and Toll-like receptor 4 signaling and maintains endotoxin tolerance. *Nat. Immunol.* 5:373.
40. Chuang, T. H., and R. J. Ulevitch. 2004. Triad3A, an E3 ubiquitin-protein ligase regulating Toll-like receptors. *Nat. Immunol.* 5:495.
41. Bartfai, T., M. M. Behrens, S. Gaidarova, J. Pemberton, A. Shivanyuk, and J. Rebek, Jr. 2003. A low molecular weight mimic of the Toll/IL-1 receptor/resistance domain inhibits IL-1 receptor-mediated responses. *Proc. Natl. Acad. Sci. U.S.A.* 100: 7971.
42. McCoy, S. L., Kurtz, S. E., MacArthur, C. J., Trune, D. R, and Hefeneider, S. H. 2005. Identification of a Peptide Derived from Vaccinia Virus A52R Protein That Inhibits Cytokine Secretion in Response to TLR-Dependent Signaling and Reduces In Vivo Bacterial-Induced Inflammation. *Journal of Immunology,* 174: 3006-3014.

What is claimed is:

1. An isolated polypeptide, consisting of:
   (a) the amino acid sequence set forth as SEQ ID NO: 16, the amino acid sequence set forth as SEQ ID NO: 17, or the amino acid sequence set forth as SEQ ID NO: 18; or
   (b) the amino acid sequence set forth as SEQ ID NO: 16, the amino acid sequence set forth as SEQ ID NO: 17, or the amino acid sequence set forth as SEQ ID NO: 18, covalently linked to the transducing amino acid sequence set forth as SEQ ID NO: 22.

2. The isolated polypeptide of claim 1, optionally modified with a fluorescent label.

3. The isolated polypeptide of claim 1, consisting of the amino acid sequence set forth as SEQ ID NO: 16, the amino acid sequence set forth as SEQ ID NO: 17, or the amino acid sequence set forth as SEQ ID NO: 18.

4. The isolated polypeptide of claim 1, consisting of the amino acid sequence set forth as SEQ ID NO: 16, the amino acid sequence set forth as SEQ ID NO: 17, or the amino acid sequence set forth as SEQ ID NO: 18 covalently linked to the transducing amino acid sequence set forth as SEQ ID NO: 22.

5. A pharmaceutical composition comprising an effective amount of the polypeptide of claim 1 and a carrier.

6. A method of inhibiting Toll Like Receptor (TLR)-induced cytokine secretion to a subject in need thereof, comprising:
administering to the subject in need thereof, an effective amount of the isolated polypeptide of claim 1,
thereby inhibiting the Toll Like Receptor (TLR)-induced cytokine secretion.

7. The method of claim 6, comprising administering to the subject an effective amount of a peptide consisting of the amino acid sequence set forth as SEQ ID NO: 16, the amino acid sequence set forth as SEQ ID NO: 17, or the amino acid sequence set forth as SEQ ID NO: 18, covalently linked to the transducing amino acid sequence set forth as SEQ ID NO: 22; thereby inhibiting Toll Like Receptor (TLR)-induced cytokine secretion.

8. The method of claim 6, wherein the peptide consists of the amino acid sequence set forth as SEQ ID NO: 16, the amino acid sequence set forth as SEQ ID NO: 17, or the amino acid sequence set forth as SEQ ID NO: 18.

9. A method of reducing or inhibiting Toll Like Receptor (TLR)-induced inflammation, comprising: administering to a subject in need thereof, an effective amount of:
a) a peptide consisting of the amino acid sequence set forth as SEQ ID NO: 16, the amino acid sequence set forth as SEQ ID NO: 17, or the amino acid sequence set forth as SEQ ID NO: 18; or
b) a peptide consisting of the amino acid sequence set forth as SEQ ID NO: 16, the amino acid sequence set forth as SEQ ID NO: 17, or the amino acid sequence set forth as SEQ ID NO: 18, covalently linked to the transducing amino acid sequence set forth as SEQ ID NO: 22;
thereby reducing or inhibiting Toll Like Receptor (TLR)-induced inflammation.

10. The method of claim 9, wherein the inflammation is caused by a bacteria.

11. The method of claim 9, wherein the bacteria is *Streptococcus pneumoniae*.

12. The method of claim 9, wherein the subject has otitis media.

13. The method of claim 9, wherein the TLR is one or more of TLR 2, TLR3, TLR4, TLR5 and TLR9.

14. The method of claim 13, wherein the TLR is TLR2.

15. The method of claim 13, wherein the TLR is TLR3.

16. The method of claim 13, wherein the TLR is TLR4.

17. The method of claim 13, wherein the TLR is TLR5.

18. The method of claim 13, wherein the TLR is TLR9.

19. The method of claim 6, wherein the TLR is one or more of TLR 2, TLR3, TLR4, TLR5 and TLR9.

20. The isolated polypeptide of claim 1, consisting of:
(a) the amino acid sequence set forth as SEQ ID NO: 16; or
(b) the amino acid sequence set forth as SEQ ID NO: 16 covalently linked to the transducing amino acid sequence set forth as SEQ ID NO: 22.

* * * * *